(12) United States Patent
Chu

(10) Patent No.: US 9,943,391 B2
(45) Date of Patent: Apr. 17, 2018

(54) MEDICAL DEVICE AND METHOD FOR DELIVERING AN IMPLANT

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 635 days.

(21) Appl. No.: 14/201,321

(22) Filed: Mar. 7, 2014

(65) Prior Publication Data

US 2014/0275752 A1    Sep. 18, 2014

Related U.S. Application Data

(60) Provisional application No. 61/777,213, filed on Mar. 12, 2013.

(51) Int. Cl.
*A61B 17/04* (2006.01)
*A61F 2/00* (2006.01)
(Continued)

(52) U.S. Cl.
CPC ........ *A61F 2/0045* (2013.01); *A61B 17/0469* (2013.01); *A61B 17/0625* (2013.01);
(Continued)

(58) Field of Classification Search
CPC ............ A61B 17/0469; A61B 17/0625; A61B 2017/06009
See application file for complete search history.

(56) References Cited

U.S. PATENT DOCUMENTS 6,575,897 B1 *  6/2003  Ory ................ A61F 2/0045
                                                        600/30
9,144,483 B2 *  9/2015  Chu ................ A61B 17/0401
(Continued)

FOREIGN PATENT DOCUMENTS

WO    2014164868 A1    10/2014
WO    2014164868 A3    12/2014

OTHER PUBLICATIONS

Invitation to Pay Additional Fees and Partial Search Report for PCT Patent Application No. PCT/US2014/023660, dated Aug. 28, 2014, 6 pages.

(Continued)

*Primary Examiner* — Samuel Gilbert
(74) *Attorney, Agent, or Firm* — Brake Hughes Bellermann LLP

(57) ABSTRACT

The present invention discloses a medical device that includes an elongate member, needle, needle deployment mechanism, and a head portion. The elongate member has a proximal portion, distal portion and a lumen defined along the elongate member. The needle deployment mechanism is disposed at least partially within the lumen. The head portion includes a tip portion that includes a front throat region, an opening, and a needle receiving portion. The front throat region includes a front edge and a lateral edge. The opening is defined by the lateral edge of the front throat region. The needle moves in and out of the device through the opening in a direction along the front edge of the front throat region. The needle receiving portion can be configured to capture the needle.

18 Claims, 19 Drawing Sheets

(51) Int. Cl.
*A61B 17/062* (2006.01)
*A61B 17/00* (2006.01)
*A61B 17/06* (2006.01)
*A61B 90/00* (2016.01)

(52) U.S. Cl.
CPC .............. *A61B 2017/00805* (2013.01); *A61B 2017/0608* (2013.01); *A61B 2090/036* (2016.02)

(56) References Cited

U.S. PATENT DOCUMENTS

2002/0173800 A1    11/2002  Dreyfuss et al.
2003/0233108 A1*  12/2003  Gellman ............ A61B 17/0469
                                                                   606/144
2010/0280530 A1    11/2010  Hashiba

OTHER PUBLICATIONS

International Search Report and Written Opinion for PCT Patent Application No. PCT/US2014/023660, dated Oct. 17, 2015, 13 pages.
International Preliminary Report on Patentability for PCT Patent Application No. PCT/US2014/023660, dated Sep. 24, 2015, 9 pages.

\* cited by examiner

MEDICAL DEVICE AND METHOD FOR DELIVERING AN IMPLANT

CROSS-REFERENCE TO RELATED APPLICATION

This application is a Nonprovisional of, and claims priority to, U.S. Patent Application No. 61/777,213, filed on Mar. 12, 2013, entitled "MEDICAL DEVICE AND METHOD FOR DELIVERING AN IMPLANT", which is incorporated by reference herein in its entirety.

FIELD

The present invention generally relates to medical devices and procedures, and particularly to devices and methods for delivery and placement of implants in a patient's body for the treatment of pelvic organ prolapse.

DESCRIPTION OF THE RELATED ART

Pelvic organ prolapse is an abnormal descent or herniation of the pelvic organs. A prolapse may occur when muscles and tissues in the pelvic region become weak and can no longer hold the pelvic organs in place correctly.

Treatment for symptoms of the pelvic organ prolapse can include changes in diet, weight control, and lifestyle. Treatment may also include surgery, medication, and use of grafts or implants to support the pelvic organs.

Sacrocolpopexy is one such surgical technique that may be used to repair pelvic organ prolapse. This can be performed, such as, by using an open abdominal technique or with the use of minimally invasive surgery such as laparoscopy. The technique may include suspension of the apical portion of vagina (or sometimes the vaginal cuff after a hysterectomy) using an implant such that the technique may generally recreate the natural anatomic support or otherwise provide support to the vagina. In an example, a portion of the implant can be fixed to the apical portion of the vagina and a second portion of the implant can be fixed to the sacrum.

The procedure for implant fixation may require several knots of a suture, generally located over such as the apical portion of the vagina to securely fasten the implant to the vaginal walls. In an example, each of the suture knots may include several layers of knotting one over other which can be time consuming and complicated. Also, since the vaginal walls are thin, there may be a chance that the vaginal walls may get penetrated or damaged when using a laparoscopic needle such as through an abdomen.

Thus, in light of the above, there is a need for a device and method for placing an implant so as to reduce complexity and the time required to complete the procedure of implant fixation and also avoid damage to or penetration of the vaginal walls.

SUMMARY

In an embodiment, the invention discloses a medical device. The medical device includes an elongate member, a needle, a needle deployment mechanism, and a head portion. The elongate member has a proximal portion, a distal portion and a lumen defined along the elongate member. The needle can be disposed within the lumen of the elongate member. The needle deployment mechanism can be disposed at least partially within the lumen for moving the needle along the elongate member. The head portion includes a tip portion, and the head portion can be provided at the distal portion of the elongate member. The head portion includes a front throat region, an opening, and a needle receiving portion. The front throat region can be provided at the tip portion. The front throat region can have a front edge and a lateral edge. The front throat region defines an open space bounded between the lateral edge and the front edge to receive a bodily tissue therein. The opening can be defined by the lateral edge of the front throat region. The opening can extend from the lumen of the elongate member such that the needle moves in and out of the device through the opening in a direction along the front edge of the front throat region. The needle receiving portion can be configured to capture the needle.

In an embodiment, the invention discloses a medical device. The medical device includes an elongate member, a needle, a needle deployment mechanism, and a head portion. The elongate member has a proximal portion, a distal portion and a lumen defined along the elongate member. The needle can be disposed within the lumen of the elongate member. The needle deployment mechanism can be disposed at least partially within the lumen for moving the needle along the elongate member. The head portion includes a tip portion, and the head portion can be provided at the distal portion of the elongate member. The head portion further includes a front throat region, a second throat region, an opening, and a needle receiving portion. The front throat region can be provided at the tip portion. The front throat region can have a front edge and a lateral edge. The front throat region defines an open space bounded between the lateral edge and the front edge. The second throat region is provided sidewise on the head portion with respect to the front throat region and defines an open space for receiving a body tissue therein. The opening can be defined by the lateral edge of the front throat region. The opening can extend from the lumen of the elongate member such that the needle moves in and out of the device through the opening, in a direction along the front edge of the front throat region. The needle receiving portion can be configured to capture the needle.

In an embodiment, the invention discloses a method for placing an implant. The method includes inserting a medical device inside the body of a patient. The medical device includes an elongate member, a needle disposed within the elongate member, and a head portion. The head portion includes a front throat region having a front edge and lateral edge such that the front throat region defines an open space bounded between the front edge and the lateral edge. The method includes contacting the front throat region to a first bodily tissue. The method includes advancing the needle of the medical device, loaded with a suture, toward the needle receiving portion so as to cause the needle to extend through an opening in a direction along the front edge and penetrate through the implant and a portion of the first bodily tissue. The opening is defined by the lateral edge. The method includes retracting the needle from the needle receiving portion.

BRIEF DESCRIPTION OF THE FIGURES

The invention and the following detailed description of certain embodiments, thereof, may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating vaginal prolapse. However, the invention may be equally employed for other treatment purposes such as pelvic organ prolapse or other pelvic disorders such as incontinence. As described below in various illustrative embodiments, the invention provides systems, methods, and devices employing a medical device configured to deliver or place an implant within a patient's body to support pelvic organs for the treatment of pelvic organ prolapsed or other pelvic disorders.

The term patient may be used hereafter for a person who benefits from the medical device or the methods disclosed in the present invention. For example, the patient may be a person whose body is operated with the use of the medical device disclosed by the present invention in a surgical treatment. For example, in some embodiments, the patient may be a human female, human male or any other mammal.

The terms proximal and distal described in relation to various devices, apparatuses, and components as discussed in the subsequent text of the present invention are referred to with a point of reference. The point of reference, as used in this description, is a perspective of an operator. The operator may be a surgeon, a physician, a nurse, a doctor, a technician, and the like who may perform the procedure of delivering and placing the bodily implants into the patient's body as described in the present invention. The term proximal refers to an area that is closest to the operator. The term distal refers to an area that is farthest from the operator.

Figure 1:
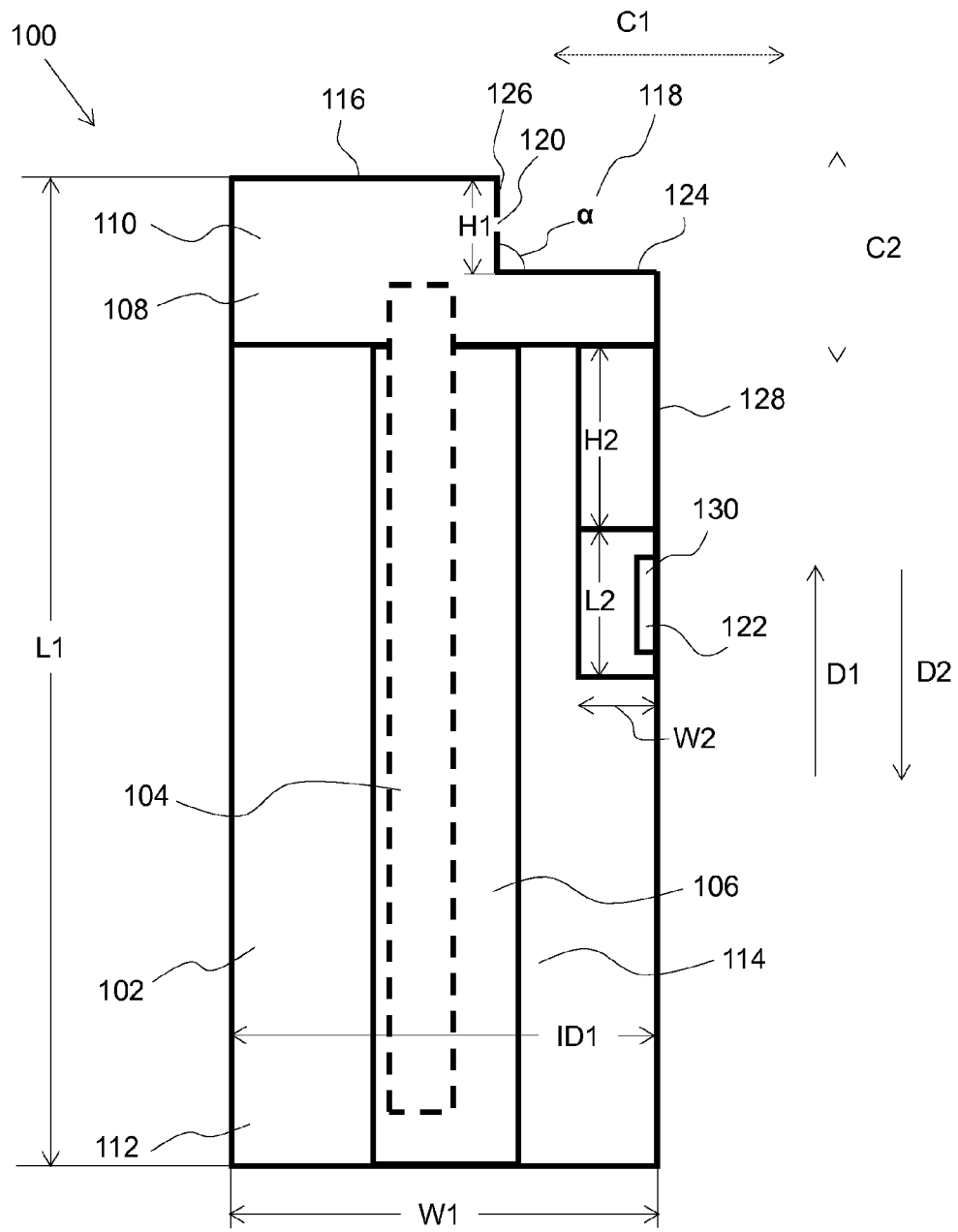
FIG. 1 is a schematic diagram of a medical device for placing an implant within a patient's body, in accordance with an embodiment of the present invention.

FIG. 1 is a schematic diagram of a medical device 100. In various embodiments, the medical device 100 is configured to deliver an implant within a patient's body or place or fix an implant such as by placing sutures through the implant and bodily tissues. The medical device 100 includes an elongate member 102, a needle 104, a needle deployment mechanism 106 and a head portion 108. The needle 104 and the needle deployment mechanism 106 are at least partially disposed within the elongate member 102. The head portion 108 can be provided at or removably coupled to a portion of the elongate member 102.

The elongate member 102 includes a distal portion 110 and a proximal portion 112 with a length L1 of the elongate member 102 extending between the distal portion 110 and the proximal portion 112 longitudinally. In accordance with various embodiments, the length L1 of the elongate member 102 can vary based on the requirements. In various embodiments of the invention, a portion of the length L1 defines a working length (not shown) of the medical device 100. The working length may be defined as a portion of the medical device 100 that can be inserted into the patient's body during the surgical procedure. In some embodiments of the invention, the working length is different from the length L1 of the elongate member 102 and the working length can range from about 9 cm to about 45 cm (approximately 3.5 inches to 17.7 inches). In various other embodiments, the working length can be different based on the requirements. The elongate member 102 defines a width W1. The width W1 may vary based on requirements. In some embodiments, the width W1 may vary along the length L1 of the elongate member 102.

The elongate member 102 defines a lumen 114 extending from the proximal portion 112, running across the length L1 of the elongate member 102 and culminating at the distal portion 110 of the elongate member 102. The lumen 114 defines an inner diameter ID1 of the elongate member 102. The lumen 114 of the elongate member 102 is configured to receive and house at least some other elements and portions of the medical device 100. For example, the elongate member 102 can be configured to house at least a portion of the needle deployment mechanism 106 and the needle 104 within a space formed within the lumen 114.

The elongate member 102 further includes a handle (not shown) that is configured to be held by an operator while performing a surgical procedure. In some embodiments, the handle forms an integral part of the elongate member 102 and extends from the elongate member 102 proximally. In some other embodiments, the handle may be a separate component and can be mechanically coupled to the elongate member 102 at the proximal portion 112. In some embodiments of the invention, the handle is provided with a thumb-tab to increase the efficiency of the handle. A physician or a user can hold the handle by placing his finger or thumb on the thumb-tab.

The distal portion 110 of the elongate member 102 includes or is coupled to the head portion 108. The head portion 108 includes a tip portion 116, a front throat region 118, an opening 120 defined by the front throat region 118 and a needle receiving portion 122. In some embodiments, the front throat region 118 is disposed at another location along the elongate member 102. For example the front throat region may be disposed at a location proximal of the distal portion or the distal most portion of the elongate member.

In an embodiment, the tip portion 116 includes the front throat region 118. The front throat region 118 can be defined in a direction parallel to a lateral axis C1 of the medical device 100. The front throat region 118 includes a front edge 124 and a lateral edge 126. In some embodiments, the front edge 124 can define a substantially circular profile. In some embodiments, the front throat region 118 can define any other profile so as to facilitate the needle 104 movement toward the needle receiving portion 122.

The lateral edge 126 abuts the front edge 124 and forms a throat angle α between the lateral edge 126 and the front edge 124. In some embodiments, the throat angle α can be 90 degrees so that the front edge 124 and the lateral edge 126 are perpendicular to each other. In some embodiments, the throat angle α can be less than 90 degrees. In some embodiments, the throat angle α can be more than 90 degrees. The lateral edge 126 can have a height H1 such that the penetration depth of the needle 104 within the bodily tissue can be limited to H1.

The front throat region 118 defines an open space bounded between the front edge 124 and the lateral edge 126 to receive a bodily tissue therein. In some embodiments, the bodily tissue can be forced or prolapsed into the front throat region 118. In some embodiments, the front throat region 118 can be configured or used to suture a portion of a Y-shaped implant to an anterior and a posterior vaginal wall. In some embodiments, the front throat region 118 can be configured or used to suture a portion of a Y-shaped implant to such as a sacrum. In some embodiments, the front throat region 118 can be configured or used to suture a portion of any other type of implant to various bodily tissues such as vaginal walls, sacrum or locations proximate the sacrum, uterus, vaginal apex and other pelvic tissues.

The opening 120 can be defined by the lateral edge 126 of the front throat region 118. The opening 120 is in communication with the lumen 114 of the elongate member 102 such that the needle 104 moves in and out of the medical device 100 through the opening 120 in a direction A1 along the front edge 124 of the front throat region 118.

In some embodiments, the head portion 108 includes a second throat region 128. The second throat region 128 can be defined parallel to a longitudinal axis C2 of the medical device 100. In some embodiment, the lateral axis C1 and the longitudinal axis C2 are perpendicular or substantially perpendicular to each other, thereby orienting the front throat region 118 and the second throat region 128 perpendicular to each other. In some other embodiments, the direction of orientation of the front throat region and the second throat region may not be perpendicular. In some embodiments, the second throat region 128 can be defined between the needle receiving portion 122 and the tip portion 116. The second throat region 128 can define an open space for receiving a bodily tissue. The second throat region 128 can define a width W3 and a height H2 such that the height H2 is generally greater than the height H1 of the lateral edge 126 of the front throat region 118, thereby configuring the second throat region 128 for deeper penetration into the bodily tissue than the front throat region 118. In other embodiments, however, the height H2 of the second throat region 128 can be equal to or smaller than the height H1 of the front throat region 118. In some embodiments, the second throat region 128 can be configured or used to suture a portion of a Y-shaped implant to such as a sacrum or tissues proximate to the sacrum. In some embodiments, the second throat region 128 can be configured or used to suture a portion of any other type of implant to various bodily tissues such as vaginal walls, sacrum uterus, vaginal apex and other pelvic tissues.

The needle receiving portion 122 is provided at the head portion 108 to capture the needle 104. The needle receiving portion 122 can include a recess 130 for receiving at least a portion of the needle 104. In accordance with some embodiments of the invention, the needle receiving portion 122 can have a length L2. The length L2 of the needle receiving portion 122 defines depth of the recess 130 that the needle 104 can, at maximum, enter into the needle receiving portion 122 after contacting a surface of the needle receiving portion 122. The length L2 can vary based on the requirements. In some embodiments of the invention, the needle receiving portion 122 can have a width W2. The width W2 can vary based on the requirements. As mentioned above, the needle receiving portion 122 includes or defines the recess 130. In various embodiments, the recess 130 can be in the form of a slot, an aperture, an opening, or any other type of a hollow space on the needle receiving portion 122 such that the recess 130 is configured to receive a suture or a dart (as explained later). In some embodiments, the width W2 of the needle receiving portion 122 can be designed to accommodate multiple recesses similar to the recess 130. In some embodiments, the multiple recesses may be configured to assure the capture or securement of a needle that has been deflected slightly after being passed through bodily tissue. In some embodiments, the recess 130 can be, for example, an L-shaped slot or a T-shaped slot.

In some embodiments, the medical device 100 can be configured to place or suture a Y-shaped implant to the bodily tissue such that the front throat region 118 can be configured to suture a portion of the Y-shaped implant to the anterior and the posterior vaginal wall, and the second throat region 128 can be configured to suture a portion of the Y-shaped implant to the sacrum or tissues proximate the sacrum. In other embodiments, the medical device 100 can be configured to place or suture other types of implants also to various bodily tissues. In some embodiments, the medical device 100 may be used to suture a mesh of any shape or of any number of legs, arms or projections. For example, the medical device 100 may be used to suture a V-shaped or a U-shaped implant into bodily tissue. In some embodiments, the medical device 100 may be used to suture implants that include any number of legs, arms, or projections to bodily tissues.

In some embodiments, the medical device can include a depth adapter (not shown in FIG. 1). In some embodiments, the depth adapter is permanently or fixedly coupled within the second throat region 128 (to effectively close the second throat region 128). In other embodiments, the depth adapter can be removably fitted in the second throat region 128 and the depth of the second throat region 128 can be adjusted depending on the requirements such as depending on the height of a bodily tissue penetration needed. In some embodiments, the depth adapter may be used in the second throat region 128 such as when a bodily tissue may surround the second throat region 128 and there can be possibility of prolapse of a portion of the bodily tissue in the second throat region 128, which may not be needed. This can, for example, occur when the front throat region 118 contacts a bodily tissue such that the longitudinal axis C2 of the medical device 100 or a direction of the front throat region 118 is at an angle lesser or greater than 90 degrees (non-perpendicular) with respect to a surface or plane of the bodily tissue during contact. However, even during non-perpendicular contact in cases when there may not be a surrounding tissue nearby the second throat region 128, the depth adapter may not be necessarily needed. Therefore, in various embodiments, an operator may decide to use or not to use the depth adapter as per specific requirements.

In some embodiments, the front throat region 118 can contact a bodily tissue such that the longitudinal axis C2 of the medical device 100 or a direction of the front throat region 118 is at an angle of 90 degree with respect to a surface or plane of the bodily tissue during contact that is to say a perpendicular or straight contact of the front throat region 118 to a surface of the bodily tissue. In such cases, the penetration depth of the needle 104 into the bodily tissue can be limited to the height of the front throat region 118 and thus the penetration depth can be controlled by configuring the front throat region 118 accordingly. In such embodiments, the depth adapter may not be required in the second throat region 128. However, in some embodiments, the depth adapter may still be used though not necessary.

The medical device 100 includes the needle deployment mechanism 106 disposed at least partially within the lumen 114 for moving the needle 104 along the elongate member 102. The needle deployment mechanism 106 defines a proximal portion and a distal portion. The proximal portion of the needle deployment mechanism 106 can be coupled to the handle of the elongate member 102. The distal portion of the needle deployment mechanism 106 can be coupled to the needle 104. In some embodiments, the distal portion of the needle deployment mechanism 106 can extend into the head portion 108 of the elongate member 102. The needle deployment mechanism 106 is configured to move the needle 104 along the elongate member 102. The needle deployment mechanism 106 moves the needle 104 between a retracted position and a deployed position. In the deployed position, the needle deployment mechanism 106 causes the needle 104 to extend out of the lumen 114 of the elongate member 102 and extend out through the opening 120. Various types of actuating mechanisms may be deployed within, or coupled to the needle deployment mechanism 106 for moving the needle 104 in and out of the opening 120. The medical device 100 can be moved from the refracted state to the deployed state by actuating the needle deployment mechanism 106 along a direction D1. After being moved to the deployed state, the needle deployment mechanism 106 can be moved to the retracted state by actuating the needle deployment mechanism 106 along a direction D2 which is opposite to the direction D1. In some embodiments, the needle deployment mechanism 106 is biased to its retracted state.

In some embodiments, the retracted position of the needle deployment mechanism 106 may also be referred to as the retracted position of the medical device 100 and similarly, the deployed position of the needle deployment mechanism 106 may also be referred to as the deployed position of the medical device 100 interchangeably throughout this document, and without any scope limitations.

The medical device 100 further includes the needle 104 disposed within the lumen 114 of the elongate member 102. The needle 104 of the medical device 100 can be coupled to or disposed within the needle deployment mechanism 106. The needle 104 is configured to move toward the recess 130 of the needle receiving portion 122 while being shifted to the deployed state from the retracted state of the medical device 100. In some embodiments, the needle 104 is at least partially disposed into the lumen 114 of the elongate member 102 of the medical device 100. The needle 104 is configured to at least partially exit the lumen 114 in the deployed state and may be completely contained inside the lumen 114 in the retracted state of the medical device 100.

In some embodiments of the invention, the needle 104 is a curved needle 104. In some embodiments, the needle 104 has a substantially circular cross section. In some embodiments, the needle 104 can have a shape different than a circular cross-sectional shape. In some embodiments, the needle 104 can have a cross-sectional shape (or outer shape) of any type of a polygon. For example, the needle 104 can have a square or a rectangular cross-sectional shape (or outer profile). In some embodiments, the needle 104 can have a tapered shape and/or a tapered portion (e.g., tapered from a proximal portion to a distal portion). In such embodiments, the needle 104 can have a varying diameter or width.

In some embodiments, at least a portion of the needle 104 can be formed of a flexible material. For example, a portion of the needle 104 that remains disposed within the lumen 114 when the medical device 100 is in the retracted state can be configured to flex or bend. In some embodiments, at least a portion of the needle 104 can be formed of the flexible material so that the portion of the needle 104 can conform to a profile of the lumen 114 as the needle 104 is slidably moved within the lumen 114. In some embodiments, the needle 104 can conform to a profile of the needle deployment mechanism 106 as the needle 104 is slidably moved within the needle deployment mechanism 106. The needle may have any shaped tip useful for puncturing tissue. For example, the needle may have a standard bevel shape, multiple bevels, multipoints, or a single point.

In some embodiments, the needle 104 can be loaded with a suture coupled to a dart. The suture can be coupled to the dart at one end and the other end can be manipulated by the user (as will be explained in more detail below). The dart can be coupled to the suture at one end and the other end can be pointed. The pointed end of the dart can pierce through the bodily tissues. In some embodiments, the suture dart arrangement can be removably coupled to the needle deployment mechanism 106. In some embodiments, the suture dart arrangement can be, at least, partially disposed into the needle deployment mechanism 106. As the needle deployment mechanism 106 is actuated toward the direction D1, the needle 104 moves toward the needle receiving portion 122. The needle 104 pierces the bodily tissue placed between the tip portion 116 and the needle receiving portion 122. The suture dart arrangement that is coupled to the needle 104 is thereby effectively passed through the bodily tissue. The suture is coupled to the needle 104; therefore it will also pass through the bodily tissue along with the needle 104. In some embodiments, the dart can be permanently coupled to the suture such as to catch the dart in the needle receiving portion 122 while the medical device 100 is inside the body of the patient and pull the dart and the suture along with the medical device 100 out of the body of the patient thereafter (explained later).

In some embodiments, the suture can be braided. In some embodiments, the suture can be a monofilament. The suture can be made of medical grade polymers such as polypropylene. In some embodiments, the suture can be made of a bio-absorbable material. After the bodily tissue grows over the implant, the suture may not be further required to fixate the implant to the tissue and therefore, a bio-absorbable suture is desirable. The dart and any extra suture can be removed from the body of the patient after placing the implant such as to avoid any internal tissue injury due to presence of any pointed materials. In some embodiments, laparoscopic scissors or cutters can be used to trim the sutures.

FIGS. 2A-2E illustrate various perspective views of a medical device 200 and portions of the medical device 200 that can be used for placing or suturing a bodily implant 202 to a bodily tissue 204 inside a body of a patient. The bodily implant 202 can be sutured to the bodily tissue 204 by using a suture 206 loaded over at least a portion of the medical device 200.

Figure 2A:
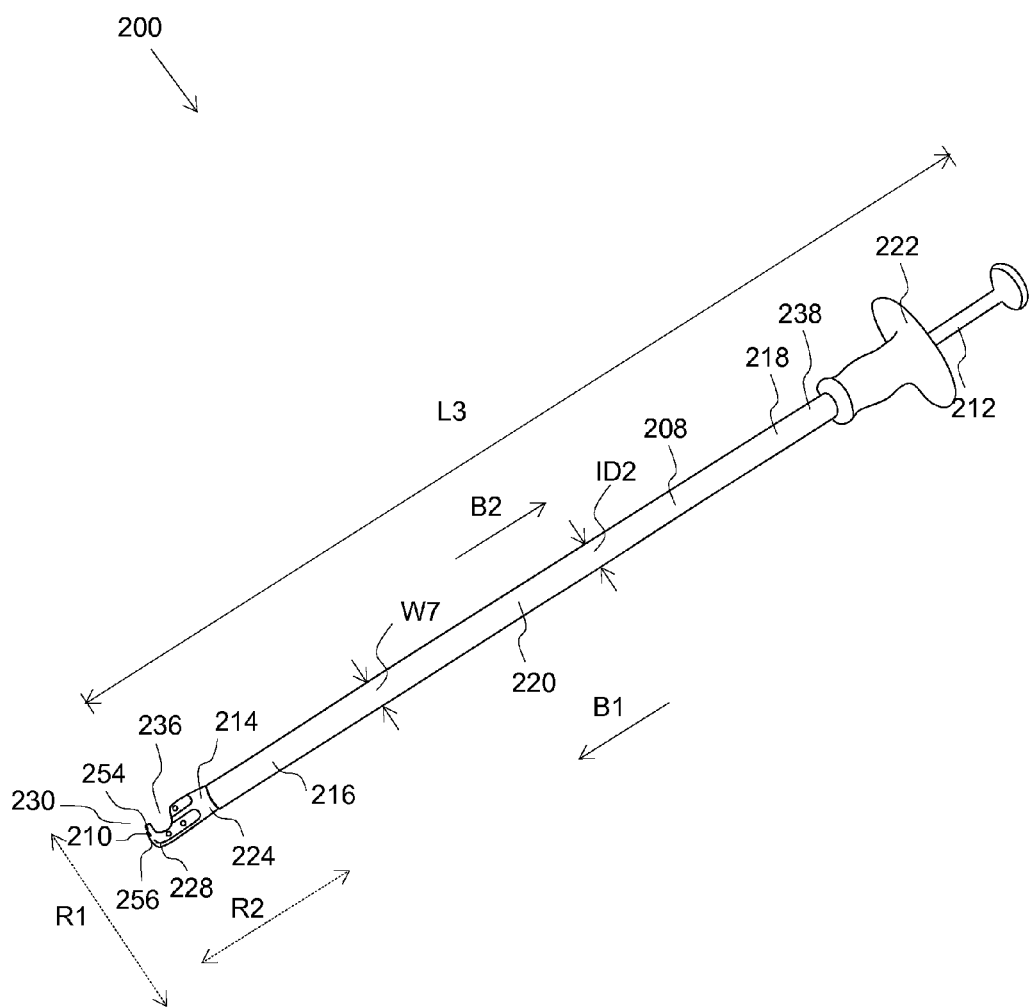
FIG. 2A is a perspective view of a medical device for placing an implant within a patient's body, in accordance with an embodiment of the present invention.

FIG. 2A is a perspective view of the medical device 200, in accordance with an embodiment of the present invention. The medical device 200 includes an elongate member 208, a needle carrier 210, a needle deployment mechanism 212 and a head portion 214. The needle carrier 210 and the needle deployment mechanism 212 are, at least, partially disposed within the elongate member 208. The head portion 214 can be provided at a portion of the elongate member 208. The medical device 200 defines a lateral axis R1 and a longitudinal axis R2. In some embodiments, the lateral axis R1 is perpendicular to the longitudinal axis R2.

The elongate member 208 includes a distal portion 216 and a proximal portion 218 with a length L3 of the elongate member 208 extending between the distal portion 216 and the proximal portion 218 longitudinally. The elongate member 208 defines a width W7. In some embodiments, the elongate member 208 is sized to be inserted or disposed within a cannula or lumen of a laparoscopic trocar. In various embodiments of the invention, the length L3 includes a working length (not shown) of the medical device 200. The working length may be defined as a portion of the medical device 200 that can be inserted into the patient's body during a surgical procedure. The elongate member 208 defines a lumen 220 extending from the proximal portion 218, running across the length L3 of the elongate member 208 and culminating at the distal portion 216 of the elongate member 208. The lumen 220 defines an inner diameter ID2 of the elongate member 208. The lumen 220 of the elongate member 208 is configured to receive and house at least some other elements and portions of the medical device 200. For example, the elongate member 208 can be configured to house at least a portion of the needle deployment mechanism 212 and the needle carrier 210 within a space formed within the lumen 220. The elongate member 208 further includes a handle 222 that is configured to be held by an operator while performing a surgical procedure.

The distal portion 216 of the elongate member 208 includes or is coupled to the head portion 214. The head portion 214 defines a proximal portion 224 and a distal portion 226. The head portion 214 includes a tip portion 228, a front throat region 230, an opening 232 defined by the front throat region 230, and a needle receiving portion 234. In accordance with the illustrated embodiment, the head portion 214 includes a second throat region 236 also.

The medical device 200 further includes the needle deployment mechanism 212 disposed at least partially within the lumen 220 for moving the needle carrier 210 along the elongate member 208. The needle deployment mechanism 212 defines a proximal portion 238 and a distal portion 240. The proximal portion 238 of the needle deployment mechanism 212 can be coupled to the handle 222 of the elongate member 208. The distal portion 240 of the needle deployment mechanism 212 can be coupled the needle carrier 210. The distal portion 240 of the needle deployment mechanism 212 can extend into the head portion 214 of the elongate member 208. The needle deployment mechanism 212 moves the needle carrier 210 between a retracted position and a deployed position. The retracted position of the needle carrier 210 may be referred to as the position where the needle carrier 210 resides inside the lumen 220 of the elongate member 208. The deployed position of the needle carrier 210 may be referred to as the position where, at least, a portion of the needle carrier 210 resides outside the lumen 220 of the elongate member 208. The needle deployment mechanism 212 includes or is coupled to an actuator 242 (shown in FIG. 2C).

The actuator 242 is disposed at the proximal portion 218 of the elongate member 208 of the medical device 200 and extends up to the needle carrier 210. In some embodiments, the actuator 242 may extend from the proximal portion 218 to a medial portion of the elongate member 208 and may also extend to the distal portion 216, in some embodiments. The actuator 242 is configured to move the needle carrier 210 out of the opening 232 at the distal portion 216 of the elongate member 208. The actuator 242 is connected to the needle carrier 210. The actuator 242 can either be in the refracted position (not shown) or in the deployed position (not shown). In the deployed position, the actuator 242 causes the needle carrier 210 to extend out of the lumen 220 of the elongate member 208. Various types of actuating mechanisms may be deployed within or coupled to the actuator 242 for moving the needle carrier 210 out of the opening 232. The medical device 200 can be configured to change its configuration from the retracted state to the deployed state by actuating the needle deployment mechanism 212 along a direction B1. After being actuated to the deployed state, the needle deployment mechanism 212 can be shifted to the retracted state by actuating the needle deployment mechanism 212 along a direction B2 which is opposite to the direction B1. In some embodiments, the needle deployment mechanism 212 is biased to its retracted state.

The medical device 200 further includes the carrier or needle carrier 210 disposed within the lumen 220 of the elongate member 208. The needle carrier 210 of the medical device 200 is coupled to the distal portion 240 of the needle deployment mechanism 212. The needle carrier 210 defines a distal portion 244 and a proximal portion 246. The proximal portion 246 of the needle carrier 210 is coupled to the actuator 242 of the needle deployment mechanism 212. The distal portion 244 of the needle carrier 210 is configured to enter the needle receiving portion 234 (discussed later) while in the deployed state. The needle carrier 210 can have a shape of various types and of various cross-sections, as discussed above in conjunction with FIG. 1. In some embodiments, the distal portion 244 of the needle carrier 210 defines a channel 252 for holding a suture or a dart (explained later). In some other embodiments, the channel 252 may extend along an entire length of the needle carrier 210.

In some embodiments, the needle carrier 210 is, at least, partially disposed into the lumen 220 of the elongate member 208 of the medical device 200. The needle carrier 210 is configured to at least, partially exit the lumen 220 in the deployed state and may be completely contained inside the lumen 220 in the retracted state of the medical device 200. In some embodiments, at least a portion of the needle carrier 210 can be formed of a flexible material, such as, discussed above in conjunction with FIG. 1.

Figure 2B:
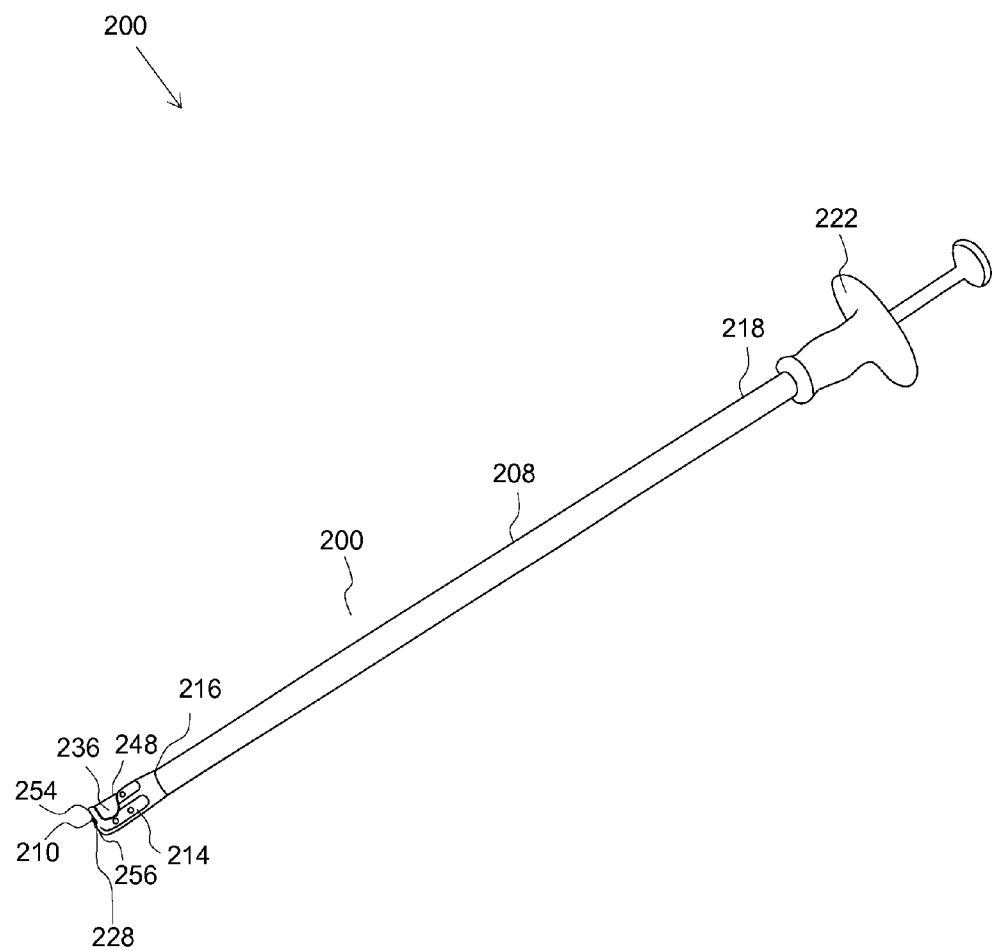
FIG. 2B is a perspective view of a medical device, along with a depth adaptor, for placing an implant within a patient's body, in accordance with an embodiment of the present invention.

FIG. 2B is a perspective view of the medical device 200 according to an embodiment. In the illustrated embodiment, the medical device 200 includes a depth adapter 248. Referring to FIG. 2B in conjunction with FIG. 2A, the medical device 200 is illustrated along with the penetration depth adapter 248. The penetration depth adapter 248 is placed in the second throat region 236 of the medical device 200. The depth adapter can be configured to be removably coupled to or placed in the second throat region 236. The front throat region 230 and the second throat region 236 are described below in conjunction with figures that show the enlarged views. While FIG. 2B illustrates the medical device 200 with a depth adapter 248 removably coupled thereto, in other embodiments, the depth adapter 248 is fixedly or permanently coupled to the medical device 200. For example, in some embodiments, the depth adapter is integrally or monolithically formed with the head or distal portion of the medical device. In such embodiments, the integrally or monolithically formed depth adapter blocks a portion of or eliminates the second throat region as describe herein with respect to the removable depth adaptor 248.

Figure 2C:
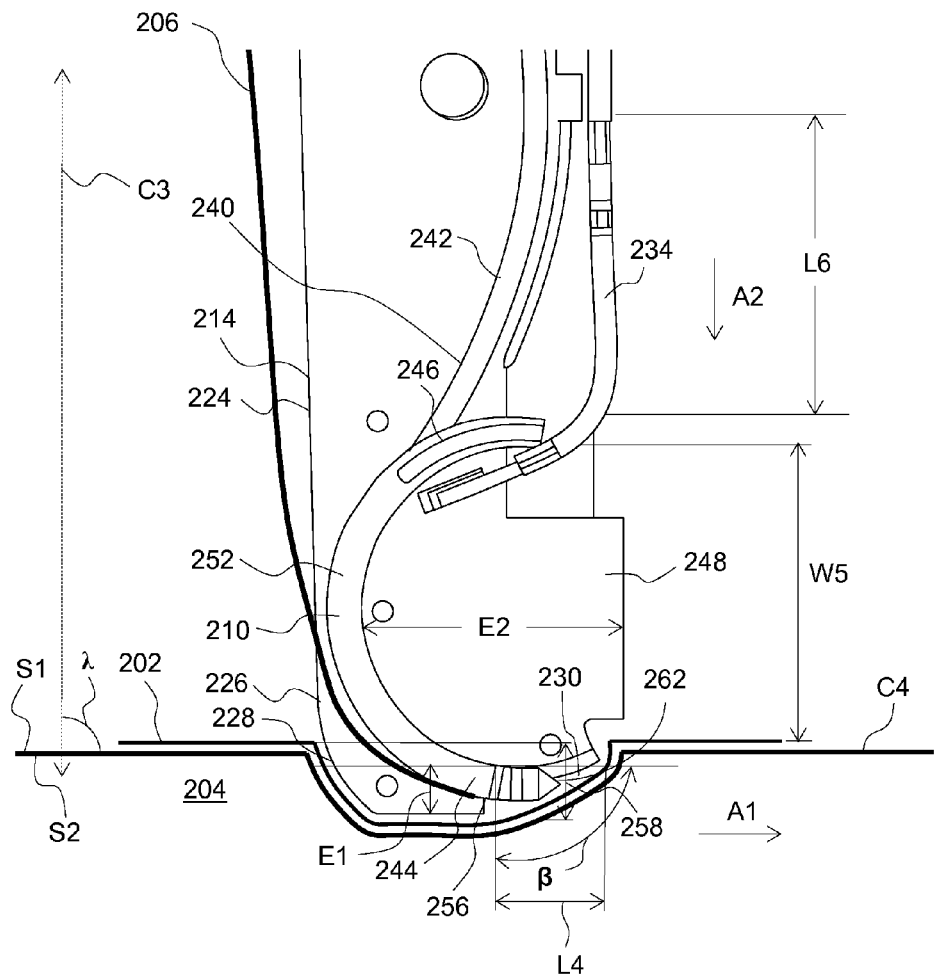
FIG. 2C is an enlarged perspective view of a head portion of the medical device of FIG. 2B engaged with a bodily tissue and an implant.
Figure 2D:
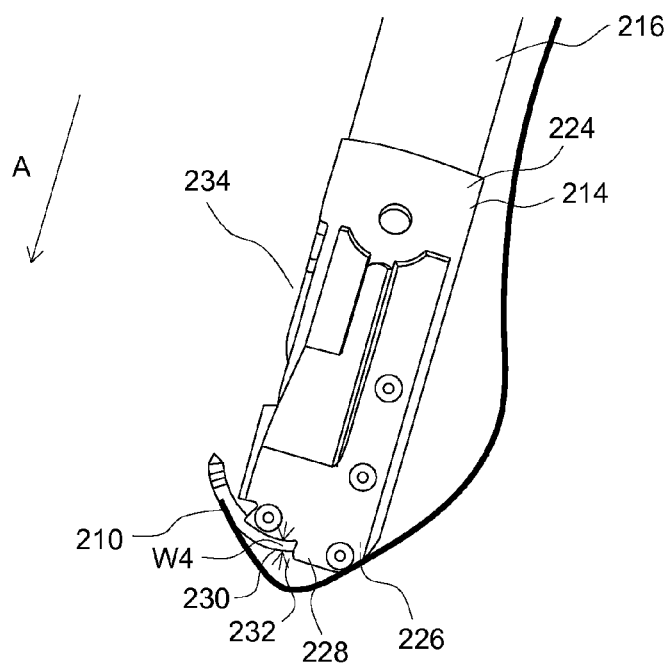
FIG. 2D is an enlarged perspective view of the head portion of the medical device of FIG. 2B in another view, in accordance with an embodiment of the present invention.

FIG. 2C is an enlarged perspective view of the head portion 214 of the medical device 200 engaged with the bodily tissue 204 and the bodily implant 202. FIG. 2D is another enlarged perspective view of the head portion 214 of the medical device 200, taken at a different angle. Referring now to FIGS. 2C and 2D in conjunction with FIGS. 2A-2B, the medical device 200 is further described below.

In some embodiments, the needle carrier 210 is mechanically connected to the actuator 242 through a carrier wire 250 and is disposed within the lumen 220 of the elongate member 208 in the tip portion 228. As mentioned above, the head portion 214 includes the tip portion 228, the front throat region 230, the second throat region 236, the opening 232 defined by the front throat region 230 and the needle receiving portion 234.

The tip portion 228 includes the front throat region 230. The front throat region 230 can be defined parallel to the lateral axis R1 of the medical device 200. The front throat region 230 includes a front edge 254 and a lateral edge 256. The front edge 254 defines a length L4 extending through the front edge 254. The front edge 254 can define a substantially circular profile.

The lateral edge 256 abuts the front edge 254 thereby forming a throat angle β between the lateral edge 256 and the front edge 254. In some embodiments, the throat angle β can be 90 degrees so that the front edge 254 and the lateral edge 256 can be perpendicular to one another. The lateral edge 256 defines a height E1 along a plane C3 of the lateral edge 256. In some embodiments, the height E1 limits a penetration depth 258 of the needle carrier 210, as will be discussed later. In some embodiments, the height E1 can be 2 mm thereby allowing the needle carrier 210 penetration into the bodily tissue 204 within a range of 1 mm to 2 mm. In some embodiments, the penetration into the bodily tissue 204 is less than 1 mm. In some embodiments, the front edge 254 and the lateral edge 256 are not perpendicular to one anther. In some embodiments, the front edge 254 or the lateral edge 256 may be curved or include a curved portion.

The front throat region 230 defines an open space bounded between the front edge 254 and the lateral edge 256 to receive the bodily tissue 204 therein. The front throat region 230 can be an empty area where the bodily tissue 204 can be forced into. In some embodiments, the bodily tissue 204 can be prolapsed into the front throat region 230. In some embodiments, the front throat region 230 can be configured or used to suture a portion of a Y-shaped implant to an anterior and a posterior vaginal wall, as discussed later.

The opening 232 can be defined by the lateral edge 256 of the front throat region 230 anywhere on the lateral edge 256. The opening 232 can be in communication with the lumen 220 of the elongate member 208 such that the needle carrier 210 moves in and out of the medical device 200 through the opening 232 in a direction A1 (shown in FIG. 2C) along the length L4 of the front edge 254 of the front throat region 230. The opening 232 can define a width W4 such that the width W4 is smaller than the height E1 of the lateral edge 256 of the front throat region 230. The opening 232 allows movement of the needle carrier 210 out of the elongate member 208.

The second throat region 236 can define an open space for receiving the bodily tissue 204. In some embodiments, the second throat region 236 can be defined parallel to the longitudinal axis R2 on the medical device 200. In some embodiments, the lateral axis R1 and the longitudinal axis R2 are perpendicular to each other. In some embodiment, the lateral axis R1 and the longitudinal axis R2 are non-perpendicular to each other. In some embodiments, the front throat region 230 and the second throat region 236 are perpendicular to each other. In some embodiments, the front throat region 230 and the second throat region 236 are non-perpendicular to each other.

In some embodiments, the second throat region 236 can be defined between the needle receiving portion 234 and the tip portion 228 such that the second throat region 236 contacts the tip portion 228 on one side and the needle receiving portion 234 on the other side. The second throat region 236 can define a width W5 and a height E2 such that the height E2 is greater than the height E1 of the lateral edge 256 of the front throat region 230, thereby, configuring the second throat region 236 for deeper penetration into the bodily tissue 204 than the front throat region 230. In some embodiments, the second throat region 236 can be configured to place or suture the bodily implant 202 over a sacrum of a body of a patient. In some embodiments, the medical device 200 can be configured to place or suture a Y-shaped implant to the bodily tissue 204 such that the front throat region 230 can be configured to suture a portion of the Y-shaped implant to the anterior and the posterior vaginal walls, and the second throat region 236 can be configured to suture a portion of the Y-shaped implant to the sacrum.

The needle receiving portion 234 is provided at the head portion 214 to capture the needle carrier 210. The needle receiving portion 234 can include a recess 260 for receiving at least a portion of the needle carrier 210. In accordance with some embodiments of the invention, the needle receiving portion 234 can have a length L6. The length L6 of the needle receiving portion 234 defines depth of the recess 260 that the needle carrier 210 can, at maximum, enter into the needle receiving portion 234 after contacting a surface of the needle receiving portion 234. The length L6 can vary based on the requirements. In some embodiments of the invention, the needle receiving portion 234 can have a width W6. The width W6 can vary based on the requirements. As mentioned above, the needle receiving portion 234 includes or defines the recess 260. In various embodiments, the recess 260 can be in the form of a slot, an aperture, an opening, or any other type of a hollow space on the needle receiving portion 234, such that, the recess 260 is configured to receive the suture 206, or a dart (as explained later). In some embodiments, the recess 260 can be, for example, an L-shaped slot or a T-shaped slot.

In accordance with some embodiments of the present invention; the plane C3 of the lateral edge 256 of the front throat region 230 can form a contact angle λ with a plane C4 of the bodily tissue 204 when the front throat region 230 contacts the bodily tissue 204 and hence, the bodily implant 202. In some embodiments, the tip portion 228 can contact the bodily tissue 204 in a direction A2 that is perpendicular to the plane C4. In some embodiments, the contact angle λ can be 90 degrees, thereby; contacting only the tip portion 228 of the medical device 200 perpendicular to the bodily tissue 204. In such cases, the penetration depth 258 of the front throat region 230 within the bodily tissue 204 is generally not greater than the height E1 of the front throat region 230. As the front throat region 230 is an empty space, therefore, the bodily tissue can be forced into it on application of a force along the height E1 at the proximal portion 224 of the elongate member 208. After the medical device 200 has penetrated to a depth equal to the height E1, the front edge 254 would stop the medical device 200 to penetrate further into the bodily tissue 204. At this point, the needle deployment mechanism 212 is actuated (as would be explained later in detail). Upon actuation, the needle carrier 210 comes out of the elongate member 208 through the opening 232 and enters the front throat region 230 and moves along the front edge 254 of the front throat region 230. Therefore, the maximum depth of the bodily tissue 204 that can be penetrated by the needle carrier 210 would be equal to or lesser than (depending upon location of the opening 232 on the lateral edge 256) the penetration depth 258 of the front throat region 230 (i.e. height E1 of the front throat region 230). In an example, the bodily tissue 204 can be a vaginal wall such as an anterior vaginal wall or a posterior vaginal wall. In normal circumstances, the vaginal wall has a thickness greater than 1 mm, therefore, the penetration depth 258 of less than 1 mm would result in a needle tissue bite, which would not let penetrate through the vaginal wall and into the vaginal lumen 220. In some embodiments, soft tissue within the vaginal lumen can be used as the anchoring or suturing tissue.

As illustrated in FIG. 2D, the needle carrier 210 can also come out of the opening 232 and move along the length L4 of the front throat region 230 in the direction A1. The suture 206 can form a loop or coil (explained later). This coil can slide over the head portion 214 along the direction B1 without catching or snagging at the front throat region 230. In the illustrated embodiment, the needle carrier 210 pushes the suture or needle that is coupled thereto through the bodily tissues 204 toward the needle catch or receiving portion 234.

Figure 2E:
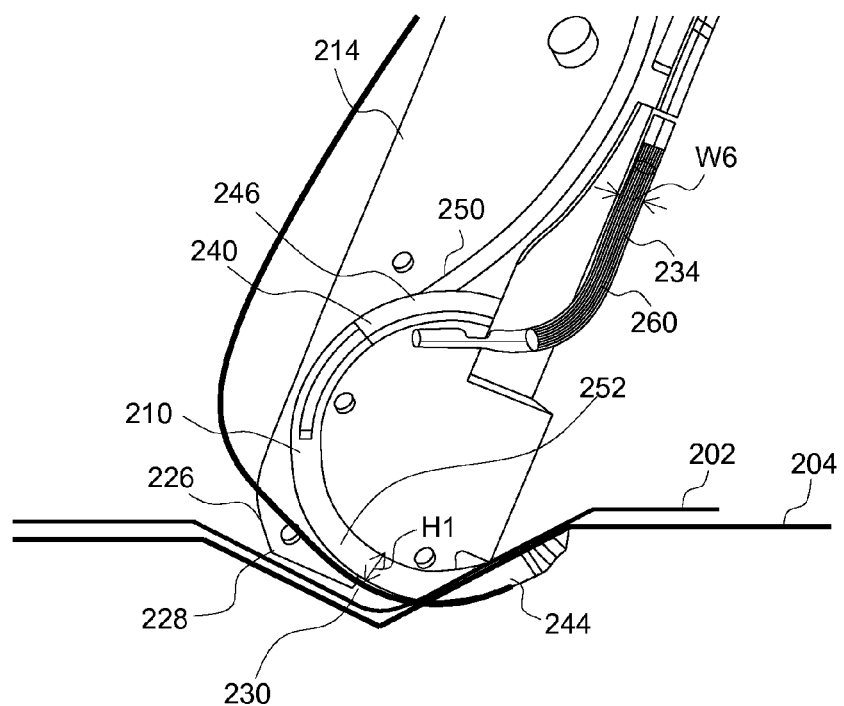
FIG. 2E is an enlarged perspective view of the head portion of the medical device of FIG. 2B with a needle pierced within a bodily tissue and an implant, in accordance with an embodiment of the present invention.

FIG. 2E is a perspective view of a portion of the medical device 200 engaged with the bodily tissue 204 and the implant 202 at a contact angle of less than 90 degrees. In some embodiments, a laparoscopic approach may be used for suturing the bodily implant 202 to the bodily tissue 204. In such cases, the contact angle can be limited by a laparoscopic cannula which may be less than 90 degrees, as illustrated in FIG. 2E. In such embodiments, the open space in the second throat region 236 can be closed so as to not allow surrounding tissues to prolapse into the second throat region 230.

As shown in FIGS. 2C-2E, a penetration depth adaptor 248 can be fitted in the second throat region 236. The second throat region 236 can be fitted with the penetration depth adapter 248 to control the needle tissue bite. This may be required such as when the second throat region 236 contacts the bodily tissues for penetration such as during suturing on the sacrum or proximate the sacrum. In some embodiments, it may be required when there are surrounding tissues proximate the second throat region 236 that may prolapse into the second throat region 236 during abutting of the front throat region 230 to the surface of the bodily tissues. For example, in some embodiments, when the contact angle λ formed by the front throat region 230 with the plane C4 of the bodily tissue 204 is less than or greater than 90 degrees, the surrounding tissues, if any, may prolapse into the second throat region 236. In some embodiments, the depth adaptor 248 can be sized for accordingly controlling the depth of penetration in the second throat region 236. In some embodiments, the depth adaptor 248 can be sized to control the depth of penetration (i.e., depth of bite) into tissues, for example, to prevent inadvertent punctures into bones, organs, tendons, or other tissues. The depth adaptor 248 can be opaque, translucent, or transparent to allow for visualization during placing the medical device 200 onto the bodily tissue 204. In alternative embodiments, the medical device 200 can include a plurality of adaptors similar to the adapter 248 that can include color coding or other markings to identify their sizes or penetrating depths. In some embodiments, the depth adaptor 248 has a smooth outer surface. In other words, in some embodiments, the outer surface of the depth adaptor 248 does not have (or is devoid of) sharp or jagged surfaces. In such embodiments, a portion of a suture, including a suture loop, may easily slide past or along the outer surface of the depth adaptor 248. In some embodiments, the depth adaptor 248 may be adjustable. For example, in some embodiments, the depth adaptor 248 may have a first portion and a second portion movable with respect to the first portion. The depth adaptor 248 may be set at a first configuration (with the first portion at one location with respect to the second portion) and may be set at a second configuration (with the first portion at a different location with respect to the second portion) to achieve or help facilitate a different amount of penetration depth.

In some embodiments, the depth adapter 248 can be removed from the device. In such embodiments, when the depth adapter 248 is removed, the height of the second throat region 236 can be greater than the height of the from throat region 230. Therefore, the second throat region 236 can define a larger empty space than the front throat region 230. This enables deeper penetration of bodily tissues through the second throat region 236 than the first throat region 230. Thus, the second throat region 236 can be used for suturing the implant to bodily tissues where a deeper penetration may be needed such as suturing to the sacrum or proximate the sacrum as discussed above. And, the front throat region 230 can be used for suturing the implant to the bodily tissues that may not require a deep penetration such as suturing the implant to the vaginal walls where a deeper penetration may not be preferred while operating laparoscopically so as to avoid piercing the vaginal walls to the lumen of the vagina.

In the illustrated embodiment of FIG. 2C, the needle carrier 210 does not penetrate through the entire thickness of the vaginal wall. The vaginal wall can have a side S1 facing the bodily implant and a side S2 facing the vaginal lumen. The suture 206 is shown entering on side S1 of the bodily tissue 204, not penetrating through side S2, and exiting back through side S1.

The front throat region 230 can control or limit the depth of penetration to the height of the front throat region 230 with or without a use of the depth adapter 248 when the front throat region 230 contacts the bodily tissues in a direction perpendicular to the direction of the plane C4 of the bodily tissue 204. However, in some embodiments, when the front throat region 230 contacts the surface of the bodily tissue at an angle, a portion of the surrounding tissues may be prolapsed into the second throat region 236. Therefore, the needle may pierce the tissue prolapsed into the second throat region 236 which may not be required. In such cases, the depth adapter 248 may be fitted in the second throat region 236 when the contact angle λ is less than or greater than 90 degrees. In some embodiments, the depth adapter 248 may be fitted in the second throat region 236 when the second throat region 236 contacts the bodily tissues such as during suturing of the implant to the sacrum or proximate tissues such as to limit the penetration depth. In such cases, the penetration depth may be controlled by adjusting the size of the depth adapter 248 or the size of the open space of the second throat region 236. In some embodiments, the front throat region 230 may include a curved region or opening.

In some embodiments, the actuator 242 is configured to actuate the medical device 200 to the deployed position from the retracted position. The actuator 242 moves the needle carrier 210 along the direction B1 and back to the retracted position from the deployed position by moving the needle carrier 210 along the direction B2. In some embodiments, actuating can include moving the needle deployment mechanism 212 or the needle carrier 210 in the direction B1. The needle carrier 210 can be moved slidably into the lumen 220 in the direction B1 along the lumen 220 and away from the proximal portion 218 of the elongate member 208, and toward the front edge 254 of the front throat region 230. The front throat region 230 provides an empty space that receives the bodily tissue 204 to be sutured with the implant 202. Generally, in some embodiments, the height E1 of the lateral edge 256 decides the penetration depth 258 of the needle carrier 210 into the bodily tissue 204. The needle carrier 210 moves out of the elongate member 208 through the opening 232 defined on the lateral edge 256 of the front throat region 230 and pierces through the bodily tissue 204. The needle carrier 210 moves along the length L4 toward the front edge 254 of the front throat region 230 while travelling inside the bodily tissue 204. Upon further actuation of the needle deployment mechanism 212, the needle carrier 210 reaches an end of the front throat region 230 and comes out of the bodily tissue 204. The height E1 of the lateral edge 256 of the front throat region 230 can control the penetration depth 258 of the needle carrier 210 into the bodily tissue 204. The needle carrier 210 can now follow a predefined pathway and travel toward the needle receiving portion 234 of the medical device 200 until the needle carrier 210 has moved into the recess 260. The recess 260 acts as a capture slot for the needle carrier 210 when it moves toward the needle receiving portion 234 on being actuated along the direction B1.

In some embodiments, actuating can include moving the medical device 200 in the direction B2. The needle carrier 210 can be moved slidably into the lumen 220 in the direction B2 along the lumen 220 and toward the proximal portion 218 of the elongate member 208, and away from the needle receiving portion 234 of the medical device 200 until the needle carrier 210 has moved out of the needle receiving portion 234 and is back into the lumen 220 of the elongate member 208 completely. In some embodiments, the actuator 242, as discussed above, can be configured to move the medical device 200 back and forth along the direction B1 and B2.

The medical device 200 can be used to place multiple sutures using a single needle carrier 210 similar to the needle carrier 210. The medical device 200 can be used for placing multiple layers of sutures over one other in order to create more robust sutures or suture knots thereby leading to effective and efficient placing of the implant 204. In some embodiments, the bodily implant 202 can be a Y-shaped implant.

The above embodiments discussed the use of the front throat region 230 for receiving the bodily tissue 204 to be sutured. In still some embodiments (e.g. where the depth adapter 248 is at least partially removed from the second throat region 236), the medical device 200 can be placed in the body in such a way that the bodily tissue 204 (to be sutured) is present within the second throat region 236. When the needle carrier 210 is actuated along direction B1, it passes through the second throat region 236 (where the bodily tissue 204 is placed) and moves toward the recess 260 of the needle receiving portion 234. As the height E2 of the second throat region 236 is greater than the height E1 of the front throat region 230 generally, the medical device 200 can have a greater penetration depth 258, in such embodiments, when the tissue is placed in the second throat region 236. The retraction of the needle carrier 210 or the medical device 200 toward the retracted state can be done in a manner as that described for other embodiments above.

Figure 3A:
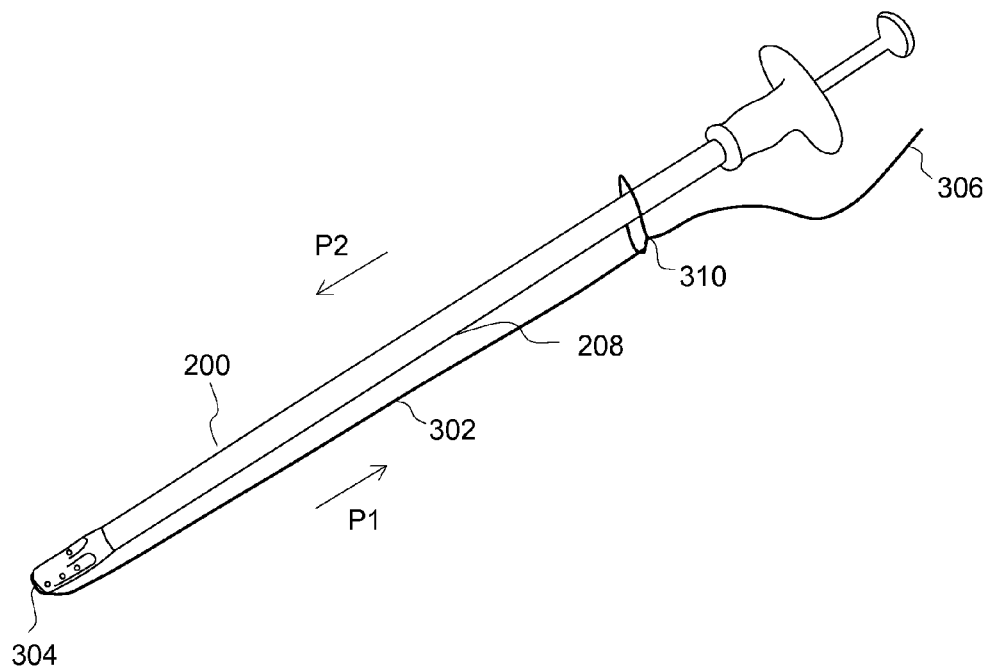
FIG. 3A is a perspective view of a medical device loaded with a suture forming a noose around the device, in accordance with an embodiment of the present invention.
Figure 3B:
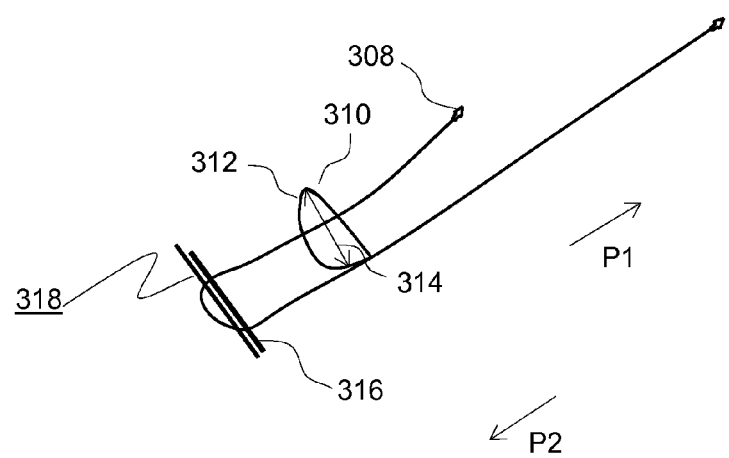
FIG. 3B is a perspective view of a suture engaged with a portion of a bodily tissue and an implant such as during implant fixation, in accordance with an embodiment of the present invention.

FIG. 3A is a perspective view of the medical device 200 loaded with a suture 302, in accordance with an embodiment of the present invention. FIG. 3B is a perspective view of the suture 302 engaged with a portion of a bodily tissue 318 and an implant 316 such as during implant fixation, in accordance with an embodiment of the present invention.

The suture 302 includes a first end 304 and a second end 306. In some embodiments, the suture 302 can include a dart 308 coupled to the first end 304 of the suture 302. The first end 304 with the dart 308 can be loaded onto the needle carrier 210. In an embodiment, the suture 302 can be wrapped around the medical device 200 so as to cross over the first end 304 and the second end 306, such as, to form a suture noose 310. In some embodiments, the suture noose 310 can be placed over the proximal portion 218 of the elongate member 208. The suture noose 310 can be formed by a suture cross-over of the two suture ends 304 and 306. In some embodiments, the suture noose 310 can be prefabricated and can be loaded onto the medical device 200 by loading the first end 304 with the dart 308 over the needle carrier 210 and passing the medical device 200 through the suture noose 310, such that, the suture noose 310 is proximate the proximal portion 218 of the elongate member 208. In some embodiments, the suture noose 310 can be positioned proximate the handle 222 of the elongate member 208.

In some embodiments, the suture noose 310 can be formed by tying the first suture end 304 and the second suture end 306 into a running knot or a loop 312, as illustrated in FIG. 3B. The running knot 312 defines a diameter 314 of the suture noose 310. The running knot 312 can be configured so that the diameter 314 decreases, making the suture noose 310 smaller when either of the first end 304 and the second end 306 of the suture is pulled along a direction P1.

The medical device 200 can be inserted inside the body of a patient by using a laparoscopic approach. When the needle deployment mechanism 212 is actuated in a direction P2, the dart 308 loaded onto the needle carrier 210 moves toward the needle receiving portion 234 along with the suture 302. The dart is received by the needle receiving portion 234 and the first end 304 of the suture 302 attached to the dart 308 passes through the bodily tissue 318. The second end 306 of the suture 302 can be pulled by the user along the direction P1. The suture noose 310, thus, can slide over the elongate member 208 along the direction P2 when the second end 306 is pulled along the direction P1. In some embodiments, the diameter 314 of the suture noose 310 decreases and the suture noose 310 slides over the elongate member 208 along the direction P2 when the second end 306 is pulled along the direction P1. The diameter 314 would decrease and the noose 310 will slide till the suture 302 cinches the bodily implant 316 to the bodily tissue 318 thereby forming a knot, referred to as slip-tie knot. The needle deployment mechanism 212 can now be actuated in the direction P1 so that the needle carrier 210 returns back in the head portion 214 of the medical device 200. The dart 308 can remain trapped inside the needle receiving portion 234 and the suturing device can be removed from the body of the patient.

In some embodiments, the slip-tie knot, as described above, can be strengthened by crossing the first end 304 and the second end 306 of the suture 302 over each other external to the body of the patient. The externally formed crossover can be pushed inside the body of the patient to form a second layer of the suture knot over the slip-tie knot. The process of forming external suture crossovers can be repeated to form multiple layers of suture knots (as illustrate later by FIGS. 8A-8C) so as to secure the bodily implant 316 to the bodily tissue 318. The two suture ends 304 and 306 can be manually trimmed so as to leave no excess material or sharp edges inside the body of the patient. In some embodiments, laparoscopic scissors or cutters can be used to trim the sutures. The medical device 200 can then move onto a new location on the bodily implant 316 and the bodily tissue 318 to place another knot with a new suture.

Figure 3C:
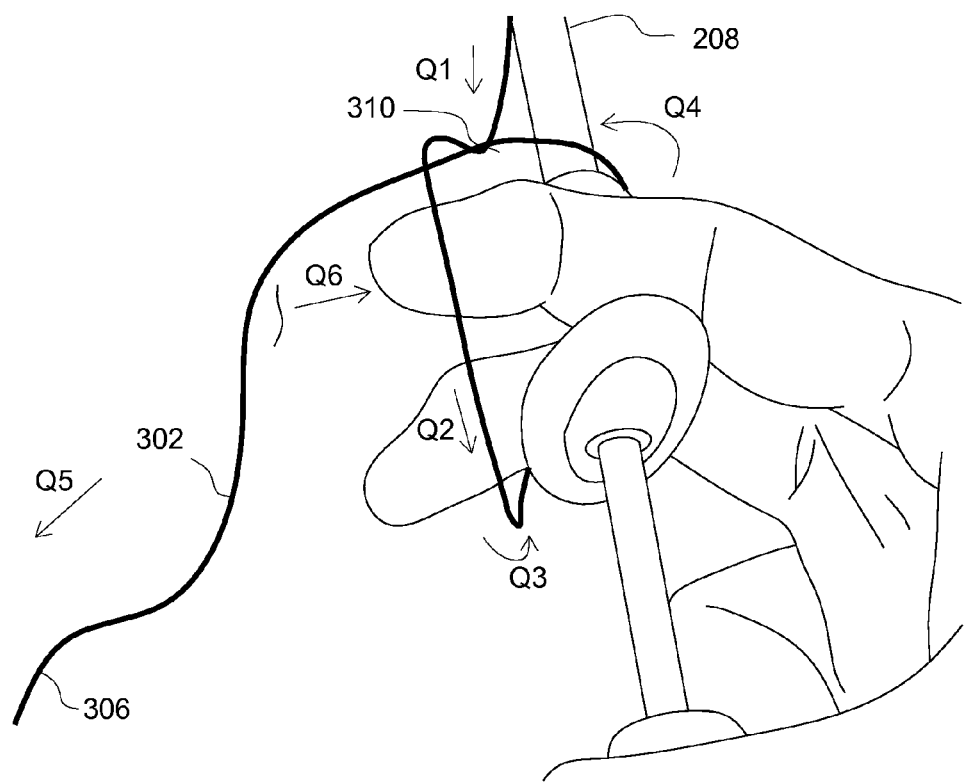
FIG. 3C is a perspective view of the suture noose formation technique, in accordance with an embodiment of the present invention.

In some embodiments, the suture noose 310 can be formed using a two finger technique, as illustrated in FIG. 3C. In accordance with the illustrated technique, the suture 302 along with the dart 308 is loaded onto the needle carrier 210 (illustrated in FIGS. 3A and 3B). The remaining portion of the suture 302 extends over the elongate member 208 along a direction Q1 and brought toward the proximal portion 218 of the elongate member 208. The suture 302 is wrapped around an index finger and a middle finger of an operator along a direction Q2. The suture 302 is then directed underneath the medical device 200, as indicated a direction Q3. The suture 302 is then brought over the actuator 242 and the elongate member 208 and crossed over a suture portion present there along a direction Q4 so as to form the suture noose 310. This makes the portion of the suture 302 proximate the second end 306 crossed over the portion of the suture 302 proximate the first end 304. The second end 306 of the suture 302 is pulled through the newly formed suture noose 310 along a direction such as Q5 to form a loop or crossover as indicated by a direction Q6. The loop formed can be similar to the lop 312 as described by FIG. 3A.

Figure 3D:
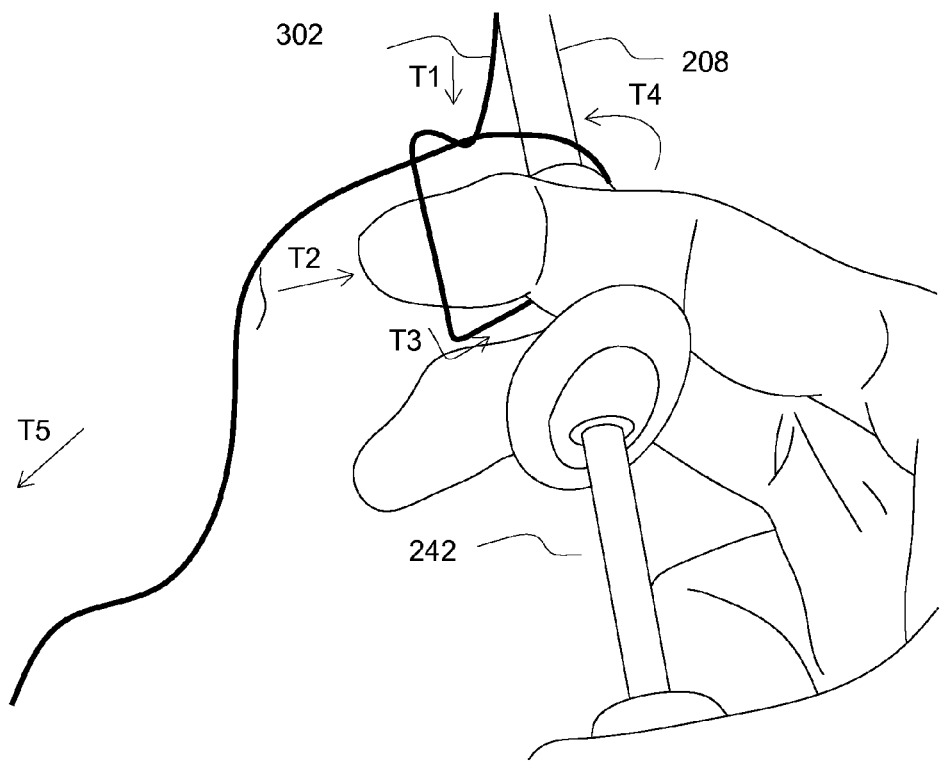
FIG. 3D is a perspective view of the suture noose formation technique, in accordance with another embodiment of the present invention.

In some embodiments, the suture noose 310 can be formed using a single finger technique as illustrated in FIG. 3D. In the illustrated technique, the suture 302 along with the dart 308 is loaded onto the needle carrier 210 (in a manner similar to illustrated in FIGS. 3A and 3B). The remaining portion of the suture 302 extends over the elongate member 208 along a direction T1 and brought toward the proximal portion 218 of the elongate member 208. The suture 302 is wrapped around an index finger of an operator along a direction T2. The suture 302 is then directed underneath the medical device 200, as indicated by arrow T3. The suture 302 is then brought over the actuator 242 and the elongate member 208 and crossed over the portion of the suture 302 present there, so as to form the suture noose 310 along a direction T4. This makes the portion of the suture 302 proximate the second end 306 crossed over the portion of the suture 302 proximate the first end 304. The second end 306 of the suture 302 is pulled through the newly formed suture noose 310 along a direction T5 to form a loop such the loop 312 or crossover. In some embodiments, a post may be used instead of the index finger of the operator. The loop formed can be similar to the loop 312 as described by FIG. 3A.

The techniques described by the way of FIGS. 3A-3D can be effectively and efficiently used to place multiple layers of suture knots so as to secure the bodily implant with the bodily tissue. In other embodiments, several other techniques may also be used to form the noose without any limitations.

Figure 4A:
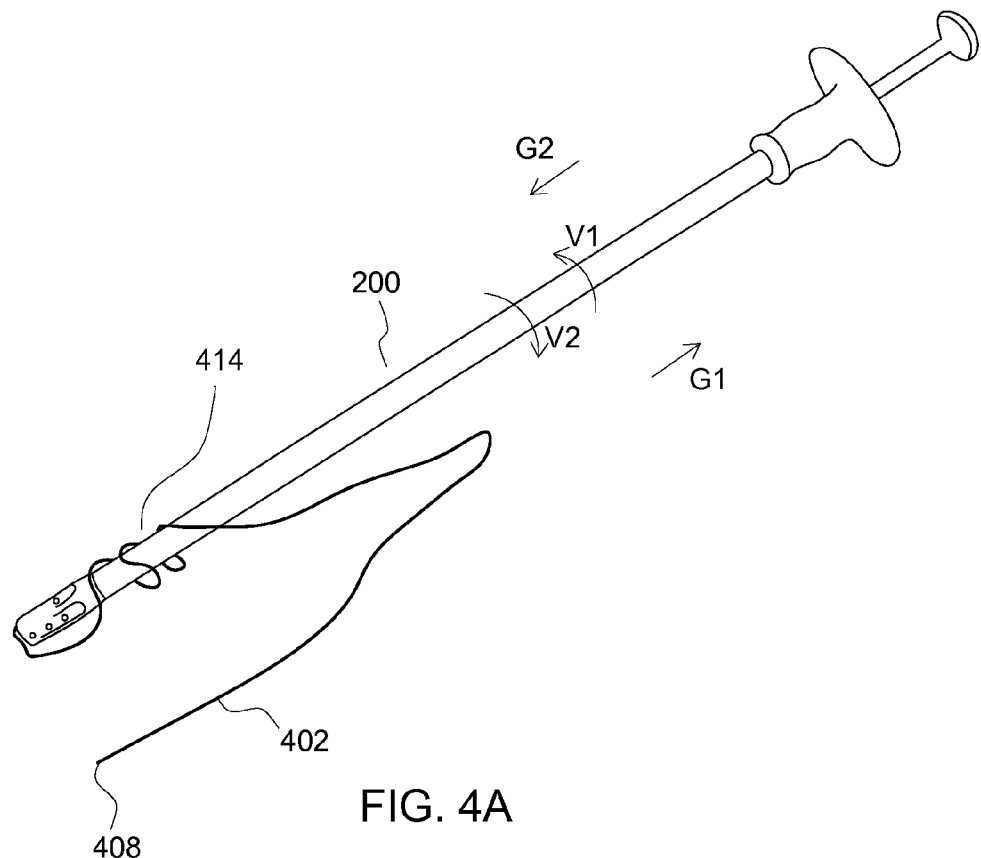
FIG. 4A is a perspective view of a medical device loaded with a suture forming a coil around the device, in accordance with an embodiment of the present invention.
Figure 4B:
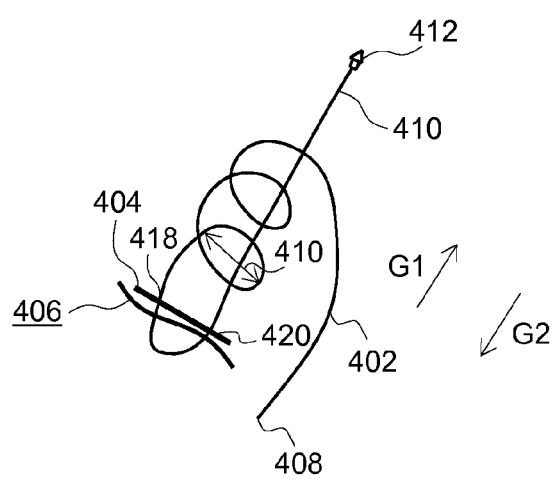
FIG. 4B is a perspective view of a suture engaged with a portion of a bodily tissue and an implant such as during implant fixation, in accordance with an embodiment of the present invention.

FIG. 4A is a perspective view of the medical device 200 loaded with a suture 402, in accordance with an embodiment of the present invention. FIG. 4B is a perspective view of the suture engaged with a portion of a bodily implant 404 (also referred to as implant 404) placed over a portion of a bodily tissue 406. In some embodiments, a single suture like the suture 402 can be used to place a series of suture knots one over another forming multiple suture knot layers or at distinct locations. The suture 402 can include a first end 408 and a second end 410. The suture 402 can be secured to the bodily implant 404 and the bodily tissue 406 by manipulating one of the first end 408 and the second end 410, while the other end can be secured to the bodily tissue 406.

In accordance with the embodiments illustrated in FIGS. 4A and 4B, the suture 402 can be used to place a knot referred to as a twist tie knot. Generally, the first end 408 of the suture is first secured to the bodily tissue 406. The second end 410 of the suture 402, along with the dart 412, can be loaded onto the needle carrier 210 of the medical device 200. The medical device 200 can then be rotated along a direction V1 or V2 so as to cause the suture 402 to be wound around the elongate member 208 and form a suture coil 414 over the elongate member 208. The suture coil 414 can define a diameter 416. In the illustrated embodiment, the suture coil 414 is shown to be formed proximate the head portion 214 of the medical device 200. However, in other embodiments, it can be positioned at other locations. The rotation of the medical device 200 can be repeated multiple times at the discretion of the operator. The rotation of the medical device 200 is generally done after insertion of the medical device 200 inside a body of a patient and before actuation of the needle deployment mechanism 212 for advancing the needle carrier 210 out of the opening 232.

FIG. 4B is a perspective view of the suture 402 with the first end 408 of the suture 402 placed inside or secured to the bodily tissue 406.

The first end 408 of the suture 402 is fixed inside the bodily tissue 406 while the second end 410 is darted and loaded onto the needle. The second end 410 advances though the bodily implant 404 and the bodily tissue 406 upon actuation of the needle deployment mechanism 212. The dart 412 enters the bodily tissue 406 at an entry site 418. The height E1 of the front throat region 230 prevents a deeper penetration of the dart 412 into the bodily tissue 406, therefore the dart 412 covers a distance equal to the height E1 inside the bodily tissue 406 and moves out of the bodily tissue 406 from an exit side 420. The bodily implant 404 can be placed over the bodily tissue 406 and therefore the dart 412 pierces the bodily implant 404 and moves toward the needle receiving portion 234. The dart 412 is then received by the needle receiving portion 234. The medical device 200 with the dart 412 inside the needle receiving portion 234 can be pulled by the operator along a direction G1 toward the outside the body of the patient. The pulling of the suture 402 along the direction G1 results in sliding of the suture coil 414 along a direction G2 toward the bodily implant 404. As the suture 402 is further pulled along the direction G1, the diameter 416 of the suture coil 414 decreases and the suture coil 414 gets closer to the bodily implant 404 till the suture coil 414 cinches the bodily implant 404 against the bodily tissue 406, thereby forming a twist tie over the bodily implant 404 for securing the bodily implant 404 over the bodily tissue 406.

The dart 412 can be retrieved from the needle receiving portion 234 with the second end 410 of the suture 402 still attached to the dart 412. This dart 412 along with the second end 410 of the suture 402 can be loaded onto the needle carrier 210 for placing another twist tie knot over the first twist tie knot so as to strengthen the suture knot. The placing of multiple coil layers can prevent the suture 402 from loosening and facilitate in efficiently placing the bodily implant 404 over the bodily tissue 404. The second end 410 of the suture 402 can be trimmed, as discussed with reference to FIGS. 3A-3E after placing the knot.

In some embodiments, the twist tie knot can be placed at different locations over the bodily implant 404 to accelerate the process of placing the implant over the bodily tissue 406. In these embodiments, the free second end 410 from previous knot many be used for placing a next knot at a different location and the fixed first end 408 may provide an anchorage for the next knot.

Figure 5:
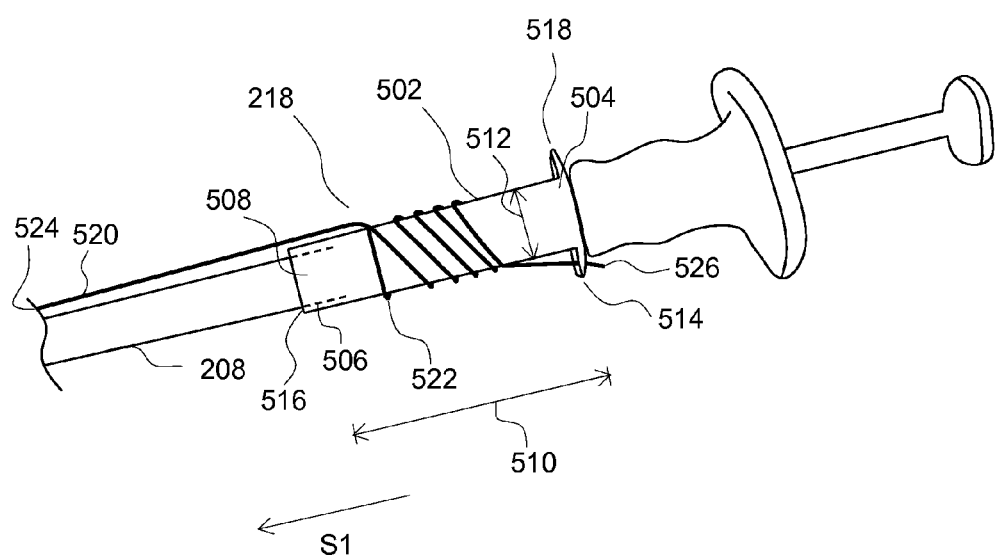
FIG. 5 is a perspective view of a portion of a cartridge loaded on a medical device, in accordance with an embodiment of the present invention.

FIG. 5 is a suture cartridge 502 used along with the medical device 200 for placing a suture 520 to a bodily implant and a bodily tissue, in some embodiments. The bodily implant and the bodily tissues can be similar to the bodily implant 202 and the bodily tissue 204 as described by FIGS. 2A-2E. The suture cartridge 502 can be loaded over the medical device 200. The suture 520 can be similar to the suture 302 or the suture 402. The suture 520 can include a first end 524 and a second end 546. In some embodiments, the suture cartridge 502 can be used to place multiple suture layers over the bodily implant 202 (similar to as described by FIGS. 3A-3D and 4A-4B) to secure the implant 22 over the bodily tissues 204. The suture cartridge 502 can be a tubular shaped or a member of any other shape. The suture cartridge 502 defines a proximal end 504, a distal end 506 and a lumen 508 extending from the proximal end 504 to the distal end 506 such that the proximal end 504 is proximate the handle 222 of the elongate member 208 of the medical device 200 when the medical device 200 is inserted in the lumen 508. The suture cartridge 502 defines a length 510 extending from the proximal end 504 to the distal end 506. The suture cartridge 502 defines a width 512. The proximal end 504 can include a first slit 514 and the distal end 506 can include a second slit 516 for the suture 520 to pass through. In some embodiments, the proximal end 504 of the suture cartridge 502 can include at least one ear 518. The ear 518 can be fabricated as a protrusion or projection at the proximal end 504 of the suture cartridge 502. In some embodiments, the ear 518 can be present circumferentially around the suture cartridge 502 at the proximal portion 504. In some embodiments, the ear 518 can be present on a portion of an outer surface of the cartridge 502 at the proximal portion 504. The ear 518 can be used by the operator while loading the suture cartridge on the elongate member 208 of the medical device 200. The ear 518 can facilitate coupling of the suture cartridge 502 with the elongate member 208. In some embodiments, the elongate member 208 can be inserted through the lumen 508 of the suture cartridge 502 and the suture cartridge 502 can be a snap fitted onto the elongate member 208 or can be fitted through other coupling and fitting mechanisms.

A pre-fabricated suture noose 522 can be loaded over the suture cartridge 502 such as around the tubular shaped cartridge. The suture noose 522 can be similar to the suture noose 310 as described by FIGS. 3A-3D. The first end 524 of the suture 520 can include the dart 308 or 412 (similar to as described by FIGS. 3A-3D and 4A-4B) and can be passed though the second slit 516 of the distal end 506 of the suture cartridge 502. The suture 520 is then extended over the elongate member 208 along a direction 51 and can be loaded onto the needle carrier 210 as illustrated in FIG. 3A. The second end 526 of the suture 520 is passed through the first slit 514 of the proximal end 504 of the suture cartridge 502 and can be used by the operator as described in FIGS. 3A-3D or FIGS. 4A-4B. In some embodiments, the suture cartridge 502 can be available as a separate device. In some embodiments, the suture cartridge 502 can be available within a kit that contains the medical device 200 and the cartridge. In some embodiments, the kit may include a plurality of such suture cartridges preloaded with the suture noose 522.

FIGS. 6A-6D illustrate some exemplary suture arrangements that may be used in conjunction with the medical device 100 or 200 in order to suture a bodily implant to a bodily tissue using procedures and techniques described in conjunction with FIGS. 3A-3D, FIGS. 4A-4B and FIG. 5. The bodily implant and the bodily tissues can be similar to the bodily implant 202, 316 or 404 and the bodily tissue 204, 318, or 406 as described by FIGS. 2A-2E, 3A-3D and 4A-4B.

Figure 6A:
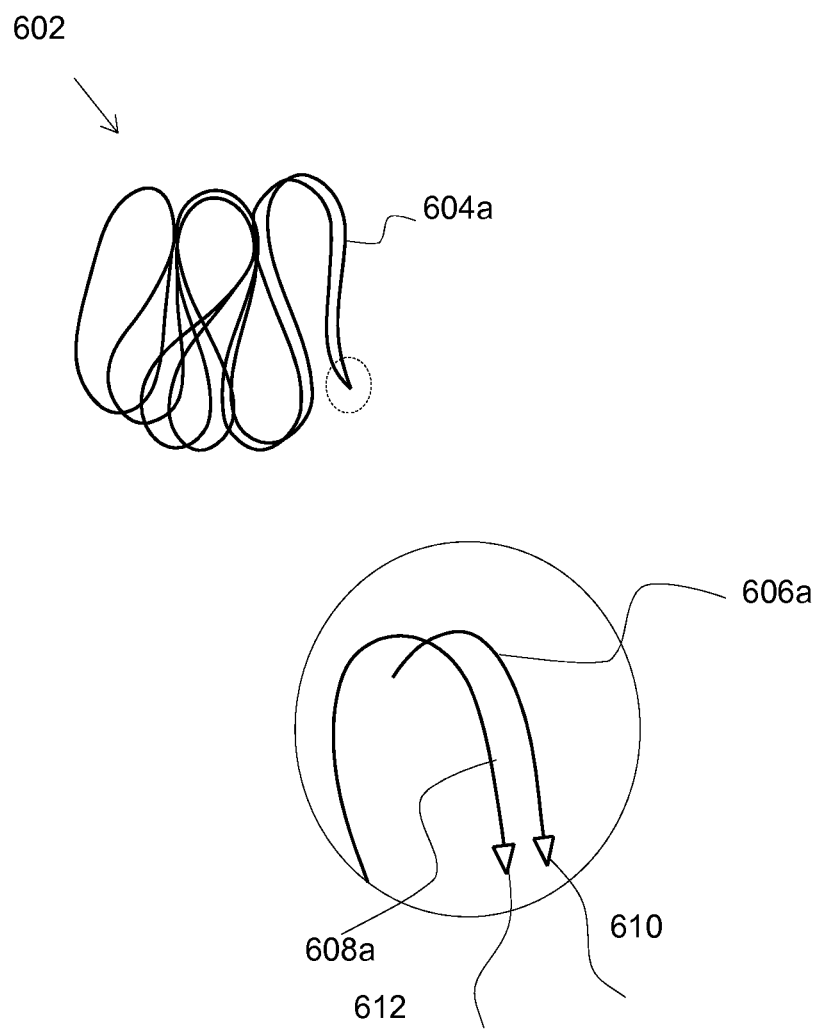
FIG. 6A is a perspective view of a suture arrangement with a dart coupled to each end of the suture, in accordance with an embodiment.

FIG. 6A is a perspective view of a suture arrangement 602, in accordance with an embodiment of the invention. The suture arrangement 602 includes a suture 604a. The suture 604a has a first end 606a and a second end 608a. The first end 606a includes a first dart 610 loaded on to it and the second end 608 includes a second dart 612 loaded on to it. Such sutures like the suture 604a may be referred to as double darted sutures. The double darted suture such as the suture 604a can be used when the suture knots require both the suture ends 606a and 608a rendered free for manipulation. For example, the first end 606a includes the first dart 610 and the second end 608a includes the second dart 612 and therefore, each of the two ends can be rendered free for further manipulation on decoupling of the respective dart 610 or 612 from the suture 604a when the darts 610 or 612 enter the needle receiving portion 234. An example of suture arrangement using the suture 604a is described by way of FIG. 7A.

Figure 6B:
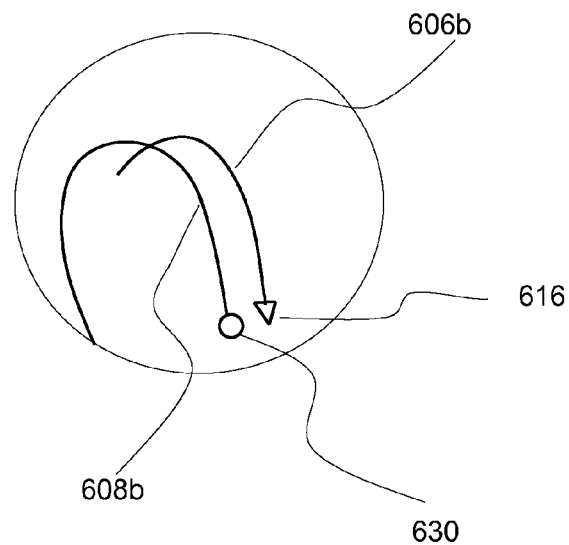
FIG. 6B is a perspective view of a suture arrangement with a dart coupled to a first end of the suture and a knot placed on a second end, in accordance with an embodiment.

FIG. 6B is a perspective view of a suture arrangement 614. The suture arrangement 614 includes a suture 604b. The suture 604b has a first end 606b and a second end 608b. The first end 606b includes a dart 616 loaded on to it and the second end 608b includes a knot 630. Such sutures like the suture 604b may be referred to as end termination sutures. The end termination sutures such as the suture 604b can be used when the suture knots require one end of the suture such as the end 604b to be free for further manipulation and another end of the suture 604b to be fixed inside the body of the patient. For example, the first end 606b includes the dart 616 and therefore, the first end 606b can be rendered free for further manipulation on decoupling of the dart 616 from the suture 604b when the dart 616 enters the needle receiving portion 234. The second end 608b includes the knot 630; therefore the second end 608b can generally get fixed inside the body of the patient. An example of suture arrangement using the suture 604b is described by way of FIG. 7C.

Figure 6C:
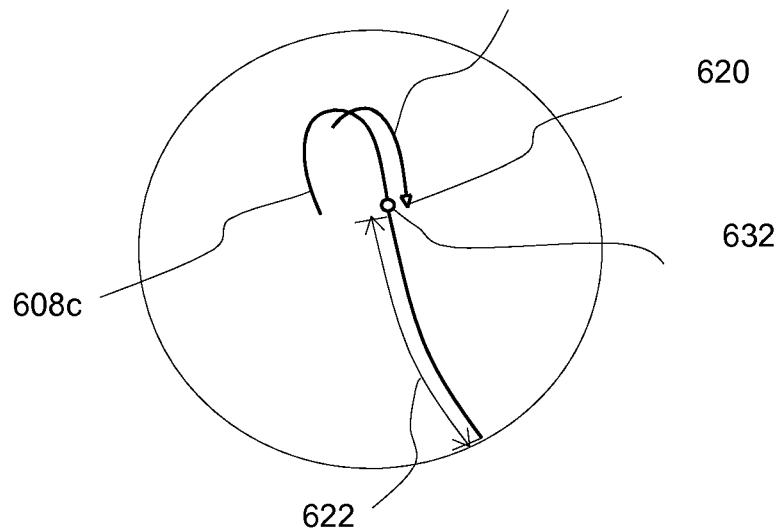
FIG. 6C is a perspective view of a suture arrangement with a dart at a first end of the suture and a knot placed on the suture proximal to a second end, in accordance with an embodiment.

FIG. 6C is a perspective view of another embodiment of suture arrangement 618. The suture arrangement 614 includes a suture 604c. The suture 604c has a first end 606c and a second end 608c. The first end 606c includes a dart 620 loaded on to it. A knot 632 is provided proximal to the second end 608c followed by a suture length 622. Such sutures like the suture 604c may be referred to as end termination sutures. In some embodiments, the suture arrangement 618 may be used for placing the slip-tie knot as described by FIGS. 3A-3D. In some embodiments, the suture arrangement 618 may be used for placing the twist tie knot as described by FIGS. 4A-4B. The suture 604c can be used to place suture knots wherein, both suture ends are free for further manipulation and one of the suture ends includes an obstruction so as to hold the suture in place. For example, the suture 604c includes the first end 606c with the dart 620 that can be decoupled from the suture 604c, thereby, rendering the first end 606c free for further manipulation. The second end 608c includes the knot 632 followed by the length 622. The knot 632 would terminate further movement of the suture 604c through the bodily tissue such as the bodily tissue 204 or 318 or 406. The length 622 would be available to the operator for further manipulation similar to the first end 606c. An example of suture arrangement using the suture 604c is described by way of FIG. 7B.

Figure 6D:
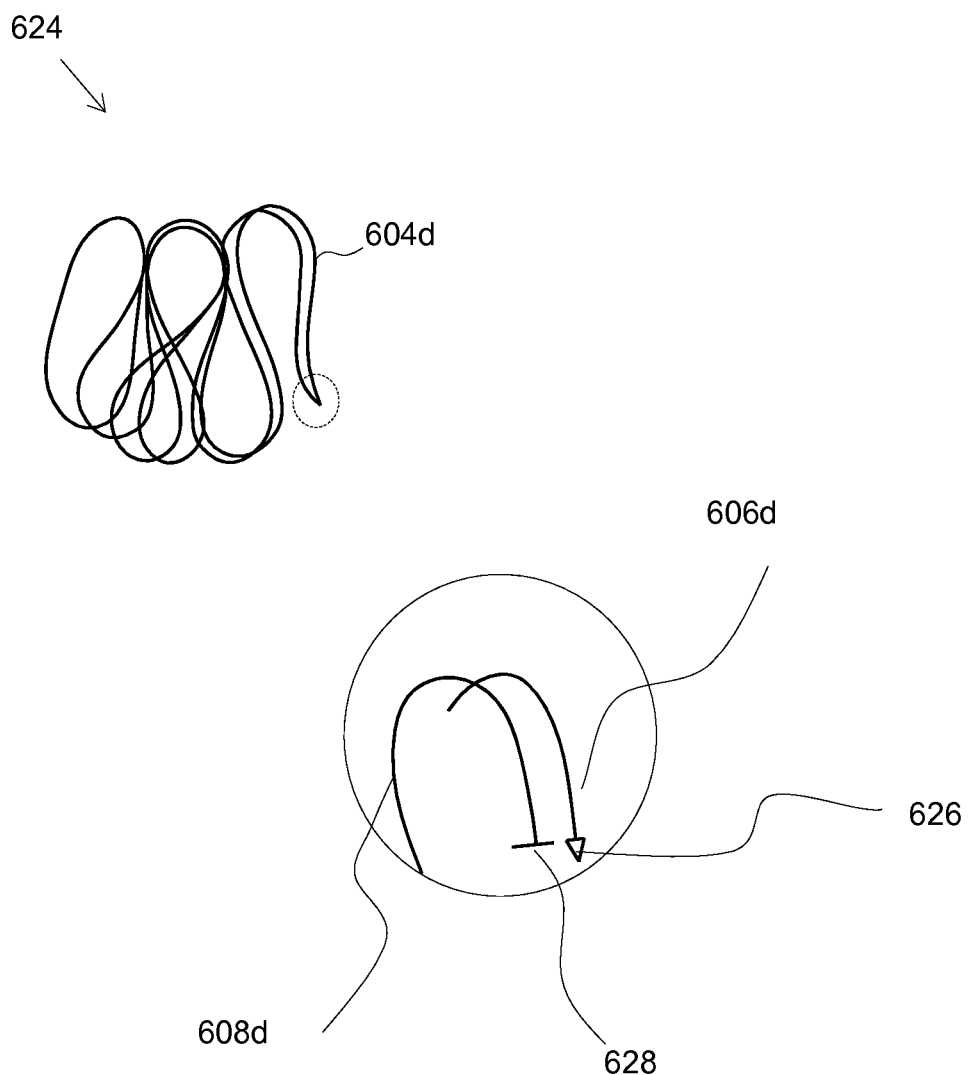
FIG. 6D is a perspective view of a suture arrangement with a dart coupled to a first end of the suture and a T-shaped second end, in accordance with an embodiment.

FIG. 6D is a perspective view of another embodiment of suture arrangement 624. The suture arrangement 614 includes a suture 604d. The suture 604d has a first end 606d and a second end 608d. The first end 606d has a dart 626 loaded on to it and the second end 608d includes a T shaped end 628. In some embodiments, the second end 608d can include any kind of termination feature that can prevent further passage of the suture 608d into the bodily tissue such as the bodily tissue 204, 318, or 406. Such sutures like the suture 604d may be referred to as end termination sutures. The end termination sutures such as the suture 604d can be used when the suture knots require one end of the suture 604d to be free for further manipulation and another end of the suture 604d be fixed inside the body of the patient. For example, the first end 606d includes the dart 626 and therefore, the first end 606d can be rendered free for further manipulation on decoupling of the dart 626 from the suture 604b when the dart 626 enters the needle receiving portion 234. The second end 608d includes the T-shaped end 628; therefore, the second end 608d can get fixed inside the body of the patient. An example of suture arrangement using the suture 604d is described by way of FIG. 7C.

In some embodiments, the suture arrangement 602, 614, 618 and 624 may be used for placing the slip-tie knot as described by FIGS. 3A-3D. In some embodiments, the suture arrangement 602, 614, 618 and 624 may be used for placing the twist tie knot as described by FIGS. 4A-4B.

Figure 7A:
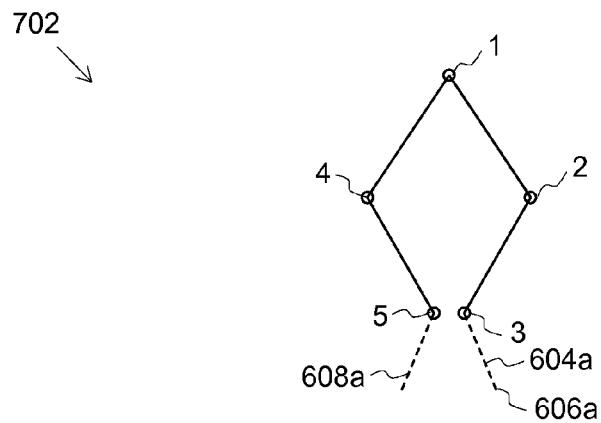
FIG. 7A is a tetrahedral pattern for placing a suture to a bodily implant, in accordance with an embodiment of the present invention.
Figure 7B:
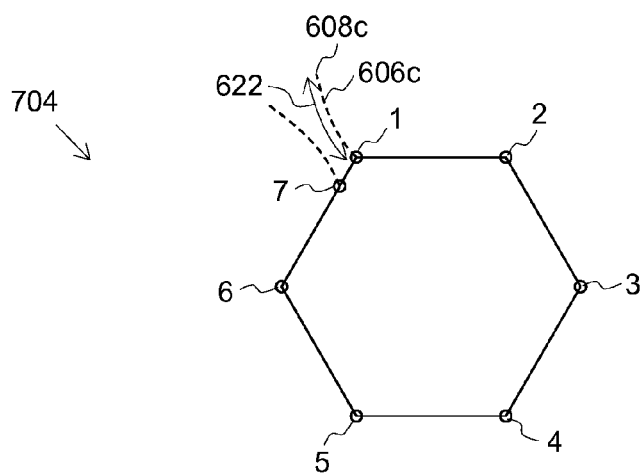
FIG. 7B is a polygonal pattern for placing a suture to a bodily implant, in accordance with an embodiment of the present invention.
Figure 7C:
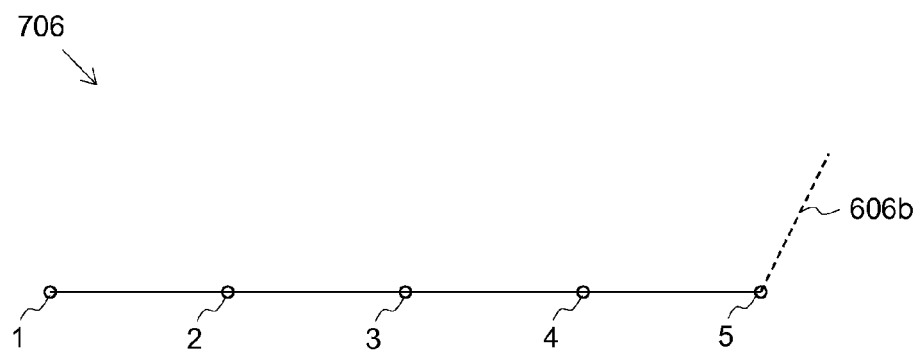
FIG. 7C is a linear pattern for placing a suture to a bodily implant, in accordance with an embodiment of the present invention.

FIGS. 7A-7C are schematic views of patterns of sutures for placing a bodily implant (such as the bodily implant 202, 316, or 404) over a bodily tissue (such as the bodily tissue 204 or 318 or 406), in accordance with an embodiment of the present invention.

FIG. 7A is a tetrahedral pattern 702 of a suture such as the suture 604a, 604b, 604c, 604d, in accordance with an embodiment of the present invention. In an embodiment, the double darted suture 604a, as described by FIG. 6A, may be used for the tetrahedral pattern 702. In the illustrated embodiment, a slip-tie knot similar to as described in FIG. 3B can be used such as at a point 1 to place a first knot. The slip-tie knot at the point 1 renders both the suture ends 606a and 608a free outside the bodily tissue such as the bodily tissue 204 or 318 or 406 for further manipulation. In some embodiments, the knot used at the point 1 may include a single knot layer. In some embodiments, the knot used at the point 1 may include multiple layers of suture knotting. Subsequent knots such as at points 2, 3, 4, and 5 can be placed using twist tie procedure that does not require any suture noose formation, such as described in FIG. 4A. The first end 606a of the suture 604a may be used to place suture knots on a series of suture points. For example, the first end 606a of the suture 604a may be used to place suture knots on points 2 and 3. The second end 608a of the suture may be used to place suture knots on a series of other suture points. For example, the second end 608a of the suture 604a may be used to place suture knots on points 4 point 5. The first end 606a and the second end 608a, after placing the suture knots on the points 3 and 5, may be crossed over externally and pushed inside, similar to placing a slip-tie knot as explained by the way of FIGS. 3A-3B. At any point in the tetrahedral pattern 702, the suture knots may include a single layer or multiple layers. In some embodiments, a medical device, different from the medical device 100 or 200, may be used for placing sutures in accordance with such suture arrangements.

FIG. 7B is a polygonal pattern 704 of a suture (such as the suture 604a, 604b, 604c or 604d), in accordance with an embodiment of the present invention. In some embodiments, the suture 604d as described by FIG. 6C may be used for the polygonal pattern 704 so as to render the length 622 from the second end 608d of the suture 604d free for manipulation. In some embodiments, a slip-tie knot similar to as described by the FIG. 3A can be placed, such as, at a point 1. The slip-tie knot at the point 1 renders both the suture ends 606d and 608d free outside the bodily tissue such as the bodily tissue 204 or 318 or 406 for further manipulation. The slip tip-knot can be placed at the point 1 using the second end 608d and the length 622 of the suture 604d can be left undisturbed external to the body, and the first end 606d can be used to place the twist tie knots (as explained by FIGS. 4A-4B) on points 2-7. After placing the twist tie knot such as at the point 7, the length 622 proximal to the second end 608d can be crossed over externally with the first end 606d. In some embodiments, the knot as described above can be strengthened by crossing the first end 606d and the second end 608d of the suture 606d over each other external to the body of the patient. The externally formed crossover can be pushed inside the body of the patient to form a second layer of the suture knot over the slip-tie knot. The process of forming external suture crossovers can be repeated to form multiple layers of suture knots so as to secure the bodily implant such 202, 316 or 404 to the bodily tissue such as the bodily tissue 204, 318, or 406. Any excess suture can be trimmed so as to not leave any extra material inside the body of the patient. At any point over the polygonal pattern 704, the suture knots may include a single layer or multiple layers. In some embodiments, the multiple layers of the suture knots may be placed by using technique as described by FIGS. 4A-4B. In some embodiments, the multiple layers of knots can be placed by using the technique as described by FIGS. 3A-3D. In some embodiments, a medical device different from the medical device 100 or 200 may be used for placing suture arrangement described above.

FIG. 7C is a linear pattern 706 of a suture (such as the 604a, 604b, 604c or 604d), in accordance with an embodiment of the present invention. In some embodiments, the sutures as described by FIG. 6B and FIG. 6D may be used for the linear suture pattern 706 so as to render the second end 608b or 608c of the suture 604b or 604c terminated inside the body of the patient. The suture knots can be placed in an open shaped pattern over the bodily implant such 202, 316 or 404. For example, the knots can be placed in a C-shape, a linear shape, or any other open arrangement. The knot can be similar to the slip-tie knot as explained by FIG. 3A placed such as at a point 1. In an embodiment, subsequent knots such as the knot at points 2-5 can be such as similar to the twist knots as explained by FIGS. 4A-4B. The suture can be tied after placing the suture knot at point 5 in case of use of the end termination suture. At any point in the linear pattern 706, the suture knots may include a single layer or multiple layers. In some embodiments, the multiple layers of the suture knots may be placed by using the technique as described by FIGS. 4A-4B. In some embodiments, the multiple layers of knots can be placed by using the technique as described by FIGS. 3A-3D. In some embodiments, a medical device, different from the medical device 100 or 200, may be used for placing the suture arrangement described above.

Figure 8A:
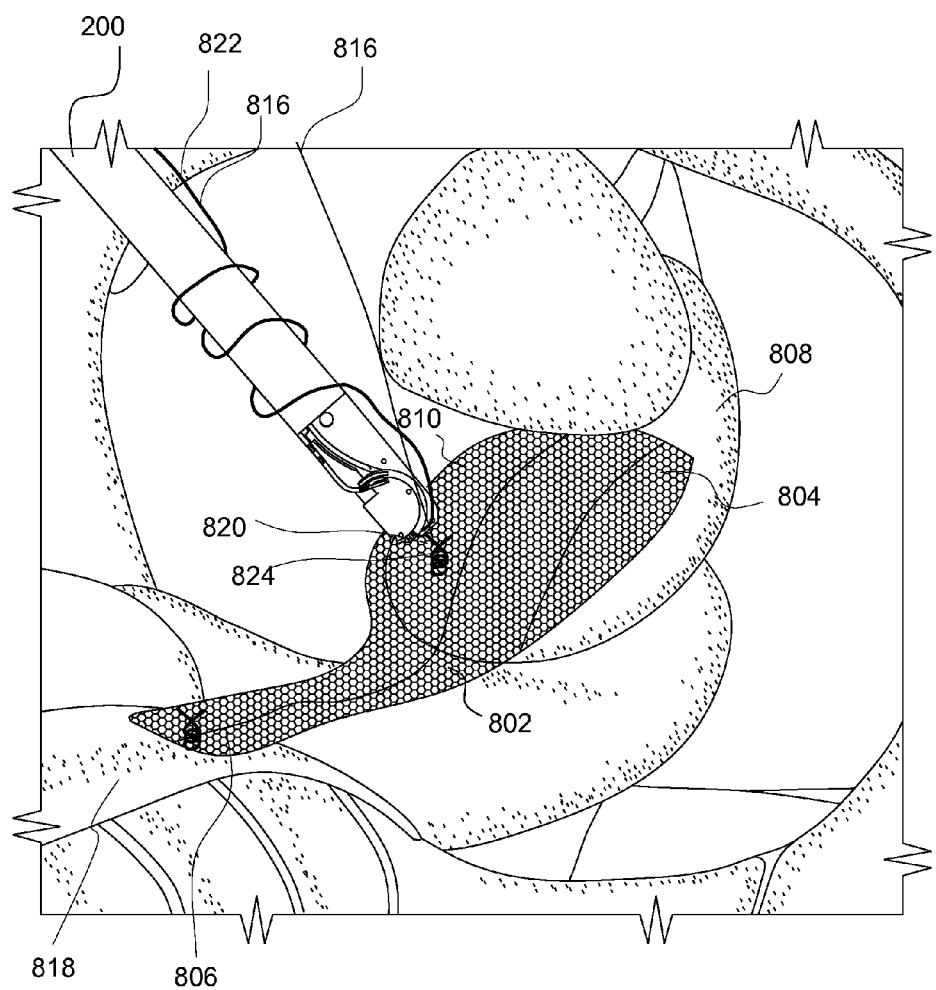
FIG. 8A is a schematic view of placing an implant within a patient's body, through a medical device, in accordance with an embodiment of the present invention.
Figure 8B:
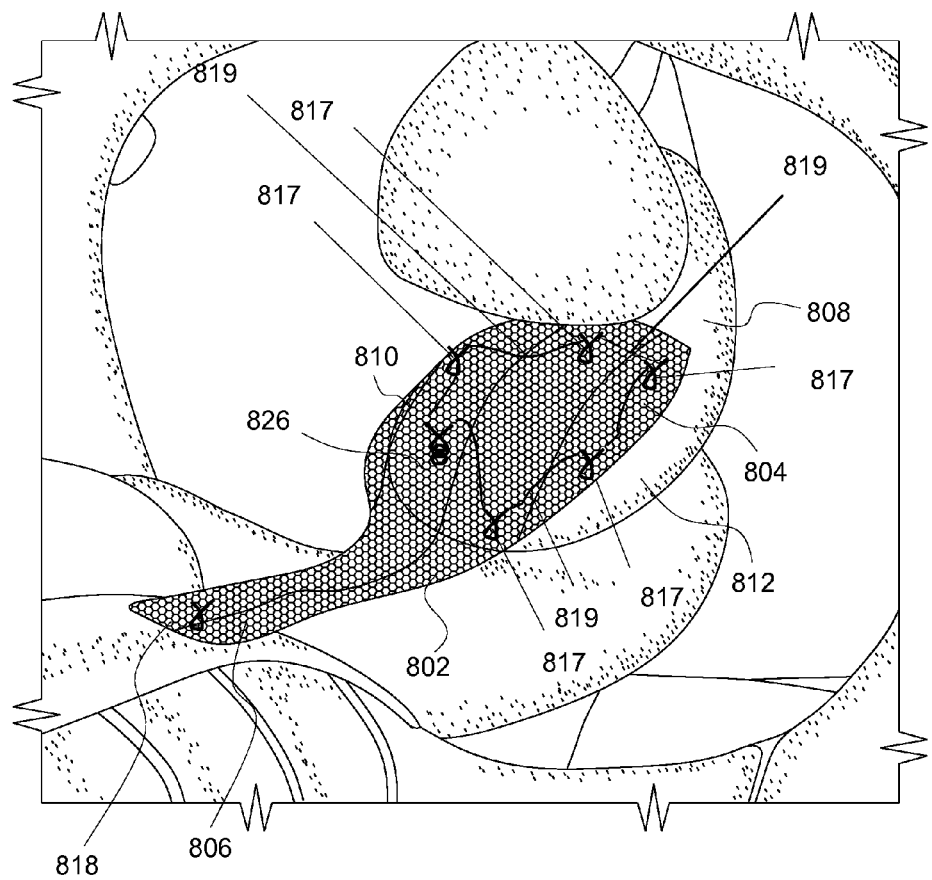
FIG. 8B is a schematic view of the placed implant of FIG. 8A within the patient's body, in accordance with an embodiment of the present invention.
Figure 8C:
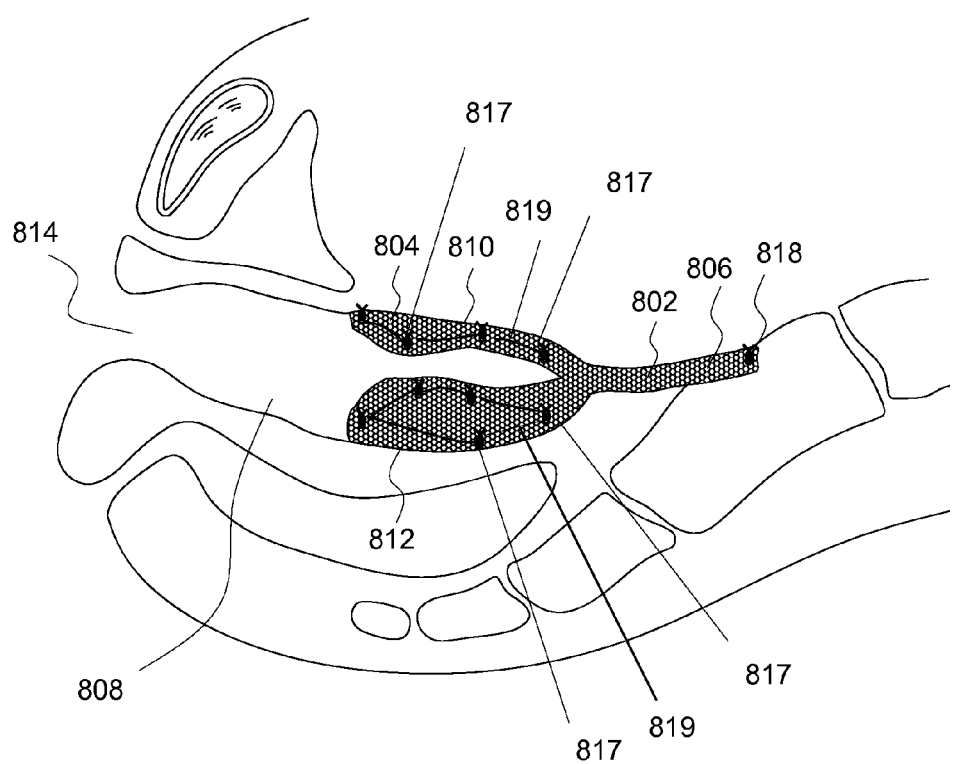
FIG. 8C is a schematic view of the placed implant of FIG. 8A within the patient's body in a different view, in accordance with an embodiment of the present invention.

FIGS. 8A-8C illustrate a method or process for placing an implant 802 within a body of a patient. FIG. 8A is a schematic view of placing an implant 802 within a patient's body using a medical device, in accordance with an embodiment of the present invention. FIG. 8B is a schematic view of the placed implant 802 within a patient's body, in accordance with an embodiment of the present invention. The bodily implant 802 is sutured to the anterior vaginal wall 810, posterior vaginal wall 812 (not visible in FIG. 8B, but visible in FIG. 8C), and the sacrum 818. FIG. 8C is a schematic view of the placed implant 600 within a patient's body in another view. As illustrated, in some embodiments, the medical device 200 is configured to suture a Y-shaped implant like the implant 802 to a body portion such that the front throat region 230 sutures a portion of the Y-shaped implant to the anterior vaginal wall 810 and the posterior vaginal wall 812, and the second throat region 236 sutures a portion of the Y-shaped implant to the sacrum 818.

The medical device 100 or 200 can be used inside a body of a patient in order to place a bodily implant 802 using techniques described above in conjunction with various figures. In some embodiments, the medical device 100 or 200 can be used for placing the bodily implant 802 inside a body of a patient for pelvic floor reconstruction. The bodily implant 802 can include a proximal portion 804 and a distal portion 806. The bodily implant 802 can be placed over the bodily tissue such that the proximal portion 804 of the implant 802 can be sutured to a vagina 808 and the distal portion 806 can be sutured to a sacrum 818 of the body of the patient.

In an embodiment, a laparoscopic approach can be used for placing and suturing of the bodily implant 802 over the vagina 808 of the patient. An anterior vaginal wall 810 and a posterior vaginal wall 812, as illustrated, are collectively referred to as the vaginal walls 810 and 812. In an embodiment, the medical device 200 can be inserted inside the body of the patient through such as a laparoscopic cannula and can be moved toward the vaginal walls 810 and 812 of the vagina 808. A suture 816 can be coupled to the needle carrier 210 of the medical device 200. The suture 816 can have a first end 820 and a second end 822. The suture 816 can be similar to the sutures 206, 302, 402, 520, 604a, 604b, 604c, 604d as described in conjunction with FIGS. 2A-7C.

In some embodiments, at least a portion of the second throat region 236 of the medical device 200 can be blocked by using a depth adapter similar to the depth adapter 248. The at least partial blocking of the second throat region 236 can avoid deeper penetration by the medical device 200 into bodily tissues such as when the second throat region contacts the bodily tissues such as to suture the implant to the sacrum or proximate tissues. In some embodiments, the at least partial blocking of the second throat region 236 may be desirable when the front throat region 230 contacts the bodily tissues and there are surrounding tissues nearby the second throat region that may prolapse into the second throat region 236 during abutting of the front region 230 to the tissues.

The front throat region 230 of the medical device 200 can be pressed against, at least, one of the vaginal walls 810 and 812. As the front throat region 230 is an empty space, a portion of bodily tissues from the vaginal walls 810 and 812 gets pressed into it. The needle deployment mechanism 212 of the medical device 200 can then be actuated so as to move the needle carrier 210, coupled to the suture 816 (and needle member), out of the opening 232 and into the vaginal wall 810 or 812 to place sutures. The height E1 of the front throat region 230 defines the penetration depth of the needle into the vaginal walls 810 and 812. The thickness of the vaginal walls 810 and 812 is generally less than 2 mm and therefore a penetration depth of less than 2 mm (or less than the thickness of the vaginal wall) would allow the needle to pierce the tissue of the vaginal walls without completely penetrating through the vaginal walls 810 and 812. This would facilitate coupling the suture 816 to the vaginal walls 810 and 812 without piercing through the vaginal walls 810 and 812.

The placement of a suture knot 824 over or into the vagina walls 810 and 812 can be done using any of the methods, techniques and arrangements described above in conjunction with various FIGS. or by using hands or using conventionally known methods. In some embodiments, each of the anterior vaginal wall 810 and the posterior vaginal wall 812 can have up to 6 suture knots like the suture knot 824 placed over the implant 802, though in other embodiments, the number of suture knots 824 can be lesser or even more than six. In some embodiments, a second knot can be placed over a suture knot 824 to further strengthen the suture knot 824. The multiple layer suture knot is depicted as 826 in the FIG. 8A.

In one embodiment, and as illustrated in FIGS. 8A-AC more than one suture know may be formed using the same suture and at different locations along the vaginal wall. In such an embodiment, the plurality of knots are coupled or connected together via a suture bridge as illustrated in FIG. 8B. As illustrated in FIG. 8A, once one knot 1010 has been placed in the vaginal wall 810 to at least partially secure the implant 802 to the body of the patient, the device 200 may be used to place another knot. Specifically, after placing the first knot 802, the device 200 can be removed from the body of the patient. The needle member may be removed from the needle catch and reloaded in the needle carrier of the device 200. The suture may also be wrapped or coiled around the shaft of the device 200 as illustrated in FIG. 8A. The device 200 may then be reinserted into the body of the patient and positioned at a location for placing another suture knot within the body of the patient. For example, the location may be proximate the first knot or disposed a distance from the first knot. In some embodiments, the device 200 is disposed within the body such that a portion of the implant 802 and a portion of the anchoring bodily tissue (such as the tissue of or proximate the vaginal wall) is disposed within the front throat region or recess 230. The device 200 can be actuated to pass the needle and suture 816 pass through the implant 802 and the anchoring bodily tissue. As described above, the needle may then be captured or contained within the needle catch. The needle carrier can then be retracted leaving the suture 816 extending through the implant 802 and the bodily tissue. The device 200 can then be refracted from the body of the patient. As the device 200 is retracted, the suture (which is coupled to the needle catch) passes through the coils or loops of the suture that are disposed about the shaft of the device. The passing of the end of the suture 816 through the coils or loops of the suture and the corresponding movement of the coils or loops toward the implant 802 form the suture knot and secure the portion of the implant 802 to the body of the patient.

As illustrated in FIG. 8B, this process can be repeated additional times to form a plurality of knots. Each of the knots is formed with the same length of suture and is therefore coupled together via a length of the suture 816. These lengths of suture may be referred to as suture bridges 819. This process can be performed any number of times to form any number of knots 817. The knots 817 may be arranged in any pattern or array (such as the patterns or arrays illustrated in FIGS. 7A-7C.

In some embodiments, the suture bridges 819 are configured to provide support to the knot structures 817. For example, in some embodiments, the sutures bridges 819 help maintain the integrity of each knot 817 and may help prevent the knots 817 from unraveling. In some embodiments, once the desired number of knots has been placed, a first end and a second end of the suture may be knotted or tied together using any known technique.

In the illustrated embodiment and as best illustrated in FIG. 8C, a separate set of knots are used to suture the implant to the anterior vaginal wall 810 and the posterior vaginal wall 812. For example, a first suture is used to form several knots to the anterior vaginal wall 810 and a different or separate suture is used to form several knots to the posterior vaginal wall 812.

After placement of the suture knots over the vaginal walls 810 and 812, in the illustrated embodiment, the medical device 200 may be used to suture a portion of the implant 802 to the sacrum or bodily tissue located proximate the sacrum. In some embodiments, after the implant 802 is coupled to the vaginal walls 810 and 812, the implant is tensioned (so as to provide the appropriate support and positioning to the vagina) and then coupled to the sacrum. In some embodiments, prior to the placement or attachment of the implant 802 to the sacrum, the medical practitioner dissects at least a portion of the peritoneum of the patient.

In some embodiments, the device 200 is used to suture or couple the implant 802 to the sacrum. For example, a knot or a series of knots (as discussed above) may be formed to couple the implant 802 to the sacrum or to tissue proximate the sacrum. In some embodiments, the second throat region 236 of the medical device 200 may be used to suture the implant 802 to the sacrum 818. In other embodiments, placing the suture knots to the sacrum 818 can be done using any known suturing or coupling method.

Figure 9:
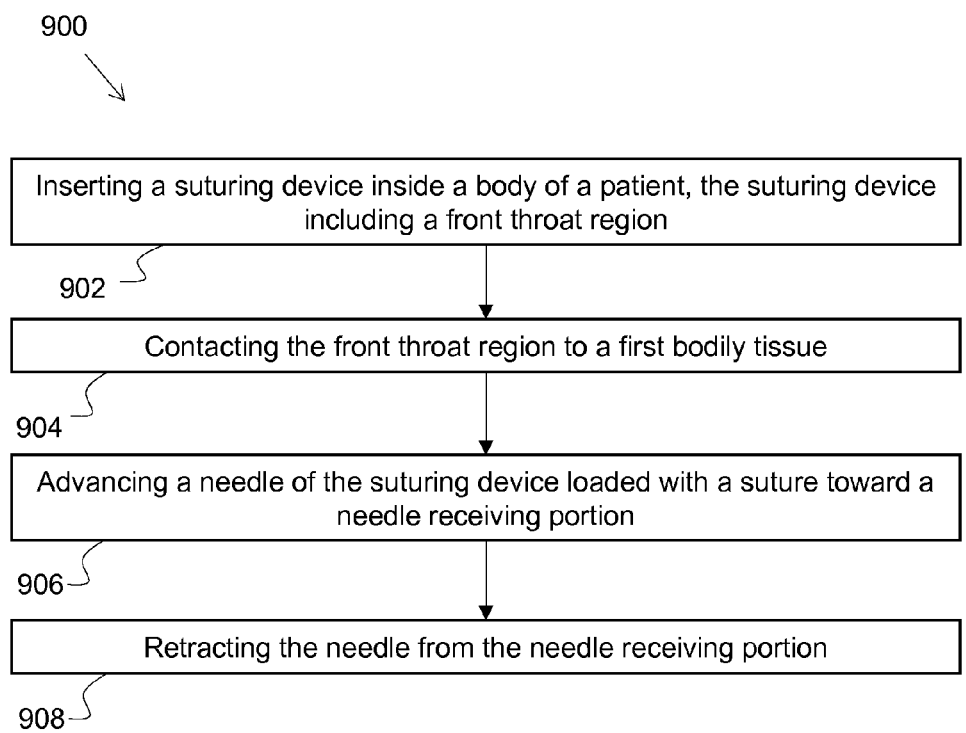
FIG. 9 is a flowchart illustrating a method of placing an implant in a patient's body, in accordance with an embodiment of the present invention.

Referring to FIG. 9; in conjunction with FIGS. 2A-2F, 3A3A-3D, 4A-4B, 5, 6A-6D, and 7A-7C, and 8A-8C, illustrates a method 900 for placing the bodily implant into the body of a patient is described.

The method 900 includes inserting a suturing device or a medical device inside a body of a patient at step 902. In some embodiments, the suturing device can be similar to the medical device 100 or medical device 200. For the purpose of explanation of the method 900, the medical device 200 has been taken into consideration. For the purpose of describing the method 800, the term suturing device is being used interchangeably with the term medical device 200. In an embodiment, the medical device 200 can be inserted into a body of a patient using a laparoscopic approach, such as, through an abdominal incision. In an embodiment, the laparoscopic approach can be used for placing and suturing of the bodily implant 802 over the vagina 808 of the patient. In an embodiment, the medical device 200 can be inserted inside the body of the patient through, such as, a laparoscopic cannula, such as, a 10 mm cannula or any other cannula and can be moved toward the vagina 808. The suture 816 can be coupled to the needle carrier 210 of the medical device 200.

The method 900 further includes contacting the front throat region 230 to a first bodily tissue at step 904. In some embodiments, the first bodily tissue can be the anterior vaginal wall 810. In some embodiments, the first bodily tissue can be the posterior vaginal wall 812. In some embodiments, the second throat region 236 of the medical device 200 can be blocked by using the depth adapter 248 for purpose of suturing the bodily implant 802 to the vaginal walls 810 and 812. In other embodiments, however, the second throat region 236 may be kept open and unblocked. The front throat region 230 of the medical device 200 can be pressed against at least one of the vaginal walls 810 and 812.

As the front throat region 230 is an empty space, a portion of bodily tissues from the vaginal walls 810 and 812 gets pressed into it.

In some embodiments, the method 800 can include contacting the second throat region 236 to a second bodily portion for fixing a portion of the implant to the second bodily tissue with the use of the second throat region 236 as described by FIGS. 8A-8C. In some embodiments, the second bodily portion can be the sacrum 818 of the body of a patient.

The method 800 includes advancing the needle of the suturing device 200 at step 906 after the front throat region 230 or the second throat region 236 contacts the bodily tissues such as the vaginal walls 810 and 812 or the sacrum 818. The needle carrier 210 can be loaded with the suture 816. The needle carrier 210 can be advanced toward the needle receiving portion 234 so as to cause the needle carrier 210 to extend through the opening 232. The needle deployment mechanism 212 of the medical device 200 can then be actuated so as to move the needle carrier 210 coupled to the suture 816 out of the opening 232 and into the vaginal wall 810 or 812 or the sacrum 818 to place sutures. The height E1 of the front throat region 230 defines the penetration depth of the needle into the vaginal walls 810 and 812 if the bodily tissue is the vaginal walls 810 and 812 and the depth adapter 248 is fitted in the second throat region 236. In such embodiments, the thickness of the vaginal walls 810 and 812 is generally less than 2 mm and therefore a penetration depth of less than 2 mm would allow needle piercing without penetrating through the vaginal walls 810 and 812. This would facilitate in placing the suture 816 over the vaginal walls 810 and 812 without piercing through the vaginal walls 810 and 812. In some embodiments, placing the suture knots over the vagina walls 810 and 812 or the 818 sacrum can be done using any of the methods, techniques and arrangements described above in conjunction with various figures.

In some embodiments, a noose similar to the suture noose 310 is slidably tied to the elongate member. In some embodiments, the method 900 includes pulling the second end 822 of the suture 816 while the needle carrier 210 advances toward the needle receiving portion 234 such that the suture noose 310 cinches with the implant 802 and forms a first knot 824 as described by FIGS. 3A-3E and illustrated in FIG. 8A. In some embodiments, the method 900 further comprises forming a second noose tied to the elongate member and pulling the second end of the suture 816 while the needle carrier 210 advances toward the needle receiving portion 234 such that the second noose cinches with the implant 802 and the first knot and forms a second knot over the first knot. This leads to formation of multiple knot layers such as 826 as described by FIGS. 3A-3E.

In some embodiments, the method 800 can further include securing the first end 820 of the suture 816 to the first bodily tissue, for example, the vaginal walls 810 or 812. The method further includes rotating the medical device 200 such that the suture 200 forms a coil around the elongate member 208, as described by FIGS. 4A-4B. The method further comprises pulling the second end 822 of the suture 816, during advancement of the needle carrier 210, in a direction B2, that is opposite the direction B1 of advancement of the needle carrier 210 such that the suture coil cinches with the implant 802 and forms the knot 824, as explained by the FIG. 4B. The method 900 can further include rotating the medical device 200 again after retracting the needle carrier 210, so as the suture to coil around the elongate member 208. The method further includes advancing the needle carrier 210 toward the needle receiving portion 234 again and pulling the second end 822 of the suture in the direction B2, opposite the direction B1 of advancement of the needle carrier 210 so as the suture coil to cinch with the implant 802 and form a second knot like the knot 824 at a different location of the first bodily tissue, as described by FIG. 4B. This leads to formation of multiple knot layers such as the knot layer 826 as described by FIGS. 3A-3E. The knots can then be tied.

Any excess suture left after placing the implant 802 can be trimmed from the body of the patient so as not leave any excess material inside the body. In some embodiments, the suture can be braided. In some embodiments, the suture can be a monofilament. The suture can be made of medical grade polymers such as polypropylene. In some embodiments, the suture can be made of a bio-absorbable material. After the bodily tissue grows over the implant, the suture may not be further required to fixate the implant to the tissue and therefore a bio-absorbable suture may be needed.

The method 800 further includes retracting the needle from the needle receiving portion after placing the suture knots. The suturing device is removed from the body after placing the suture knots.

In some embodiments, a medical device includes an elongate member having a proximal portion, a distal portion and a lumen defined along the elongate member; a needle disposed within the lumen of the elongate member; a needle deployment mechanism disposed at least partially within the lumen for moving the needle along the elongate member; and a head portion including a tip portion and provided at the distal portion of the elongate member. The head portion includes a front throat region provided at the tip portion and having a front edge and a lateral edge, the front throat region defining an open space bounded between the lateral edge and the front edge to receive a bodily tissue therein; an opening defined by the lateral edge of the front throat region and extending from the lumen of the elongate member such that the needle moves in and out of the device through the opening in a direction along the front edge of the front throat region; and a needle receiving portion configured to capture the needle.

In some embodiments, the device includes a second throat region provided in a direction substantially perpendicular with respect to the front throat region and defining an open space for receiving a bodily tissue therein. In some embodiments, the device is configured to suture an implant to a bodily tissue, wherein the front throat region is configured to suture a portion of the implant to an anterior and a posterior vaginal wall, and the second throat region is configured to suture a portion of the implant to a sacrum. In some embodiments, the implant is a Y-shaped implant In some embodiments, the height of the second throat region is greater than height of the front throat region such that the second throat region is configured for deeper needle penetration into a tissue than the front throat region. In some embodiments, the height of the front throat region is 2 millimeter (mm) or less and is configured to limit a penetration depth of the needle within a range of 1 mm to 2 mm, when the needle contacts a body tissue in a direction perpendicular to a plane of the bodily tissue. In some embodiments, the device includes a depth adapter configured to removably fit into a second throat region. In some embodiments, the depth adapter, when fitted in a second throat region, is configured to control penetration depth of the needle through the front throat region when the needle contacts a bodily tissue in a non-perpendicular direction with respect to a plane of the bodily tissue.

In some embodiments, the device is configured to be attached to a suture loaded with a dart at least at one end of the suture. In some embodiments, the suture includes a noose tied to the elongate member of the device.

In some embodiments, the device includes a cartridge having a lumen such that the elongate member is inserted within the lumen of the cartridge, and the suture is tied around the cartridge.

In some embodiments, a medical device includes an elongate member having a proximal portion, a distal portion and a lumen defined along the elongate member; a needle disposed within the lumen of the elongate member; a needle deployment mechanism disposed at least partially within the lumen for moving the needle along the elongate member; and a head portion including a tip and provided at the distal portion of the elongate member. The head portion a front throat region provided at the tip and having a front edge and a lateral edge, the front throat region defining an open space bounded between the lateral edge and the front edge; a second throat region provided in a direction substantially perpendicular with respect to the front throat region and defining an open space for receiving a body tissue therein; an opening defined by the lateral edge of the front throat region and in communication with the lumen of the elongate member such that the needle moves in and out of the device through the opening in a direction along the front edge of the front throat region; and a needle receiving portion configured to capture the needle.

In some embodiments, the device includes a depth adapter configured to be fitted within the second throat region. In some embodiments, the device is configured to suture an implant to a body portion. The front throat region is configured to suture a portion of the implant to an anterior and a posterior vaginal wall, and the second throat region is configured to suture a portion of the implant to a sacrum. In some embodiments, the implant is a Y-shaped implant. In some embodiments, the device is configured to be attached to a suture. The suture may include a dart loaded or coupled to at least at one end of the suture.

In some embodiments, a method for placing an implant includes inserting a medical device inside a body of a patient, the medical device including an elongate member, a needle disposed within the elongate member, and a head portion including a front throat region having a front edge and lateral edge such that the front throat region defines an open space bounded between the front edge and the lateral edge; contacting the front throat region to a first bodily tissue; advancing the needle of the medical device loaded with a suture toward the needle receiving portion so as to cause the needle to extend through an opening, defined by the lateral edge, in a direction along the front edge and penetrate through the implant and a portion of the first bodily tissue; and retracting the needle from the needle receiving portion.

In some embodiments, the first bodily tissue is a vaginal wall. In some embodiments, the first bodily tissue is an anterior vaginal wall. In some embodiments, the first bodily tissue is a posterior vaginal wall.

In some embodiments, the medical device includes a second throat region provided in a direction substantially perpendicular with respect to the front throat region, and the method includes contacting the second throat region to a second bodily portion for fixing a portion of the implant to a second bodily tissue with a use of the second throat region. In some embodiments, the second bodily portion is a sacrum. In some embodiments, the medical device is inserted within the body through a laparoscopic approach.

In some embodiments, the suture includes a noose that is slidably tied or coupled to the elongate member and the method includes pulling a free end of the suture while the needle advances toward the needle receiving portion such that the noose cinches with the implant and forms a first knot. In some embodiments, the method includes forming a second noose tied to the elongate member; and pulling a free end of the suture while the needle advances toward the needle receiving portion such that the second noose cinches with the implant and the first knot and forms a second knot over the first knot. In some embodiments, the method includes securing a first free end of the suture to the first bodily tissue; rotating the device such that the suture forms a coil around the elongate member; and pulling a second free end of the suture, during advancement of the needle, in a direction opposite the direction of advancement of the needle such that the suture coil cinches with the implant and forms a knot. In some embodiments, the method includes rotating the device again after retracting the needle so as the suture to coil around the elongate member; advancing the needle toward the needle receiving portion again; and pulling the second free end of the suture in a direction opposite the direction of advancement of the needle so as the suture coil to cinch with the implant and form a second knot at a different location of the first bodily tissue. In some embodiments, the method includes trimming a portion of an excess suture. In some embodiments, the method includes removing the medical device from the body.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device comprising;
   an elongate member having a proximal portion, a distal portion and a lumen defined along the elongate member;
   a needle disposed within the lumen of the elongate member;
   a needle deployment mechanism disposed at least partially within the lumen for moving the needle along the elongate member;
   a head portion including a tip portion and provided at the distal portion of the elongate member, the head portion including:
      a front throat region provided at the tip portion and a distal most portion of the elongate member, the front throat region having a front edge and a lateral edge, the lateral edge extending parallel to a longitudinal axis of the elongate member, the front edge being disposed perpendicular to the lateral edge, the front throat region defining a first open space bounded between the lateral edge and the front edge to receive a bodily tissue therein, the lateral edge having a height that limits a penetration depth of the needle;
      an opening defined by the lateral edge of the front throat region and extending from the lumen of the elongate member such that the needle moves in and out of the device through the opening of the lateral edge in a direction along the front edge of the front throat region;
      a second throat region defining a second open space, the second open space defining a larger empty space than the first open space; and a needle receiving portion configured to capture the needle.

2. The medical device of claim 1, wherein the second throat region is provided in a direction perpendicular with respect to the front throat region.

3. The medical device of claim 1, and the medical device is configured to suture an implant to the bodily tissue, wherein the front throat region is configured to suture a portion of the implant to an anterior and a posterior vaginal wall, and the second throat region is configured to suture a portion of the implant to a sacrum.

4. The medical device of claim 1, wherein a height of the second throat region is greater than the height of the lateral edge.

5. The medical device of claim 1, wherein the height of the lateral edge is 2 millimeter (mm) or less and is configured to limit a penetration depth of the needle within a range of 1 mm to 2 mm, when the needle contacts the bodily tissue in a direction perpendicular to a plane of the bodily tissue.

6. The medical device of claim 1, and including a depth adapter configured to removably fit into the second throat region.

7. The medical device of claim 6, wherein the depth adapter, when disposed within the second throat region, is configured to control penetration depth of the needle through the front throat region when the needle contacts tissue in a non-perpendicular direction with respect to a plane of the bodily tissue.

8. The medical device of claim 1, further comprising:
a suture configured to be attached to the medical device, the suture being loaded with a dart at least at one end of the suture.

9. The medical device of claim 8, wherein the suture includes a noose tied to the elongate member of the device.

10. The medical device of claim 8, and including a cartridge having a lumen such that the elongate member is inserted within the lumen of the cartridge, and the suture is tied around the cartridge.

11. A medical device comprising:
an elongate member having a proximal portion, a distal portion and a lumen defined along the elongate member;
a needle disposed within the lumen of the elongate member;
a needle deployment mechanism disposed at least partially within the lumen for moving the needle along the elongate member;
a head portion including a tip and provided at the distal portion of the elongate member, the head portion including:
 a front throat region provided at the tip, the front throat region being defined by a step from a distal most portion of the elongate member, the front throat region having a front edge and a lateral edge, the lateral edge extending parallel to a longitudinal axis of the elongate member, the lateral edge being disposed perpendicular to the front edge, the front throat region defining a first open space bounded between the lateral edge and the front edge, the lateral edge having a height that limits a penetration depth of the needle;
 a second throat region provided in a direction perpendicular with respect to the front throat region and defining a second open space for receiving a body tissue therein, the second open space defining a larger empty space than the first open space;
 an opening defined by the lateral edge of the front throat region and in communication with the lumen of the elongate member such that the needle moves in and out of the device through the opening in a direction along the front edge of the front throat region; and
 a needle receiving portion configured to capture the needle.

12. The medical device of claim 11, and including a depth adapter configured to be disposed within the second throat region, the depth adaptor configured to limit a penetration depth of the needle.

13. The medical device of claim 11, and the medical device is configured to suture an implant to a body portion, wherein the front throat region is configured to suture a first portion of the implant to an anterior and a posterior vaginal wall, and the second throat region is configured to suture a second portion of the implant to a sacrum.

14. The medical device of claim 11, and is configured to be attached to a suture, the suture further including a dart loaded at least at one end of the suture.

15. A method for placing an implant, the method comprising:
inserting a medical device inside a body of a patient, the medical device including an elongate member, a needle disposed within the elongate member, and a head portion including a front throat region, the front throat region being defined by a step from a distal most portion of the elongate member, the front throat region having a front edge and lateral edge, the front edge defining at least a portion of a most distal face of the elongate member, the lateral edge extending parallel to a longitudinal axis of the elongate member, the lateral edge being disposed perpendicular to the front edge, the front throat region defining a first open space bounded between the front edge and the lateral edge, the head portion including a second throat region defining a second open space, the second open space defining a larger empty space than the first open space, the medical device including a depth adaptor disposed within the second throat region;
contacting the front throat region to a first bodily tissue;
contacting the second throat region to a second bodily tissue such that an amount of the second bodily tissue entering the second throat region is limited by the depth adaptor;
advancing the needle of the medical device loaded with a suture toward a needle receiving portion so as to cause the needle to extend through an opening, defined by the lateral edge, in a direction along the front edge and penetrate through the implant and a portion of the first bodily tissue; and
retracting the needle from the needle receiving portion.

16. The method of claim 15, wherein the first bodily tissue is a vaginal wall.

17. The method of claim 15, wherein the first bodily tissue is an anterior vaginal wall.

18. The method of claim 15, wherein the first bodily tissue is a posterior vaginal wall.

* * * * *